(12) United States Patent
Bachmann et al.

(10) Patent No.: US 8,344,111 B2
(45) Date of Patent: Jan. 1, 2013

(54) HUMAN MONOCLONAL NICOTINE SPECIFIC ANTIBODIES

(75) Inventors: Martin Bachmann, Seuzach (CH); Monika Bauer, Zürich (CH); Roger Beerli, Adlikon b. Regensdorf (CH); Patrik Maurer, Winterthur (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 0 days.

(21) Appl. No.: 12/745,537

(22) PCT Filed: Sep. 11, 2008

(86) PCT No.: PCT/EP2008/062104
§ 371 (c)(1), (2), (4) Date: Jan. 31, 2011

(87) PCT Pub. No.: WO2009/068335
PCT Pub. Date: Jun. 4, 2009

(65) Prior Publication Data
US 2011/0123541 A1 May 26, 2011

(30) Foreign Application Priority Data

Nov. 29, 2007 (EP) .................................... 07121874
May 15, 2008 (EP) .................................... 08008993

(51) Int. Cl.
C07K 16/00 (2006.01)
A61K 39/395 (2006.01)
(52) U.S. Cl. ................ 530/387.9; 530/388.9; 424/130.1
(58) Field of Classification Search .................... None
See application file for complete search history.

(56) References Cited

U.S. PATENT DOCUMENTS
2005/0136047 A1  6/2005 Ennifar et al.

FOREIGN PATENT DOCUMENTS
| EP | 1921142 A1 | 5/2008 |
| WO | WO 02/058635 A2 | 8/2002 |
| WO | WO 03/078600 A2 | 9/2003 |
| WO | WO 2004/050032 A2 | 6/2004 |
| WO | WO 2005/040338 A2 | 5/2005 |
| WO | WO 2006/061723 A2 | 6/2006 |

OTHER PUBLICATIONS

Roiko et al. "Passive immunization with a nicotine-specific monoclonal antibody decreases brain nicotine levels but ddoes not precipitate withdrawal in nicotine-dpendent rats" Pharmacol Biochem Behav. 2009, 93(2), 105-111.*

Beerli, R.R., "Isolation of human monoclonal antibodies by mammalian cell display.", Proc. Natl. Acad. Sci. USA 105(38):14336-41, The National Academy of Sciences, US (2008).
Bjercke, R.J., "Stereospecific monoclonal antibodies to nicotine and cotinine and their use in enzyme-linked immunosorbent assays.", J. Immunol. Methods 90(2):203-13, Elsevier Science Publishers B.V., The Netherlands (1986).
Celie, P.H.N., "Nicotine and carbamylcholine binding to nicotinic acetylcholine receptors as studied in AChBP crystal structures.", Neuron 41(6):907-14, Cell Press, (2004).
Hukkanen, J., "Metabolism and disposition kinetics of nicotine.", Pharmacol. Rev. 57(1):79-115, The American Society for Pharmacology and Experimental Therapeutics, US (2005).
Isomura, S., "An immunotherapeutic program for the treatment of nicotine addiction: hapten design and synthesis.", J. Org. Chem. 66(12):4115-21, American Chemical Society, US (2001.
Keyler, D.E., "Monoclonal nicotine-specific antibodies reduce nicotine distribution to brain in rats: dose- and affinity-response relationships.", Drug Metab. Dispos. 33(7):1056-61, The American Society for Phatmacology and Experimental Therapeutics, US (2005).
Koller, D., "A high-throughput alphavirus-based expression cloning system for mammalian cells.", Nat. Biotechnol. 19(9):851-5, Nature Publishing Group, GB (2001).
Kosten, T., "Immunotherapy for the treatment of drug abuse.", Pharmacol. Ther. 108(1):76-85, Elsevier Science Pbublishers B.V., The Netherlands (2005).
LeFranc, M.-P., "IMGT unique numbering for immunoglobulin and T cell receptor variable domains and Ig superfamily V-like domains.", Dev. Comp. Immunol. 27:55-77, Elsevier Science Publishers B.V., The Netherlands (2003).
LeFranc, M.-P., "IMGT, the international ImMunoGeneTics information system®: a standardized approach for immunogenetics and immunoinformatics.", Immunome Res. 11:3, BioMed Central Ltd., GB (2005).
LeFranc, M.-P., "IMGT, the International ImMunoGeneTics Information System.", Nucleic Acids Research (33):593-597, Oxford University Press, GB (2005).
Maurer, P., "A therapeutic vaccine for nicotine dependence: preclinical efficacy, and Phase I safety and immunogenicity.", Eur J Immunol 35(7):2031-40, WILEY-VCH Verlag GmbH & Co. KGaA, DE (2005).
Pentel, P.R., "Differential effects of passive immunization with nicotine-specific antibodies on the acute and chronic distribution of nicotine to brain in rats.", J. Pharmacol. Exp. Ther. 317(2):660-6, The American Society for Pharmacology and Experimental Therapeutics, US (2006). Poulsen, "Kinetic, affinity, and diversity limits of human polyclonal antibody responses against tetanus toxoid.", J Immunol 179(6):3841-50, The American Association of Immunologists, Inc., US (2007).
Scaviner, D., "Protein displays of the human immunoglobulin heavy, kappa and lambda variable and joining regions.", Exp. Clin. Immunogenet. 16(4):234-40, S. Karger AG, CH (1999).

* cited by examiner

Primary Examiner — Maher Haddad
Assistant Examiner — James Rogers
(74) Attorney, Agent, or Firm — Sterne, Kessler, Goldstein & Fox P.L.L.C.

(57) ABSTRACT

The invention relates to recombinantly produced human monoclonalantibodies which are specifically binding nicotine and to nucleic acids encoding the same. The invention further relates to the use of such antibodies in the treatment of nicotine addiction.

20 Claims, 1 Drawing Sheet

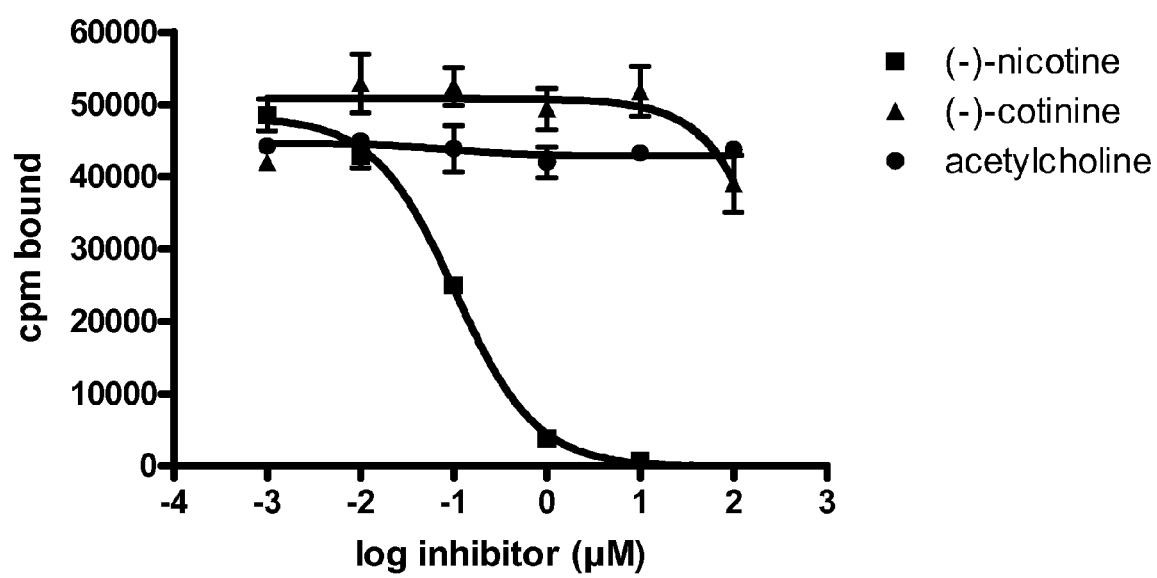

HUMAN MONOCLONAL NICOTINE SPECIFIC ANTIBODIES

REFERENCE TO SEQUENCE LISTING SUBMITTED ELECTRONICALLY

The content of the electronically submitted sequence listing (Name: sequencelisting_ascii.txt; Size: 101,553 bytes; and Date of Creation: Jan. 31, 2011) filed with the application is incorporated herein by reference in its entirety.

FIELD OF THE INVENTION

The invention relates to recombinantly produced human monoclonal antibodies which are specifically binding to nicotine and which are capable of preventing the passage of nicotine from the blood into the brain. The invention further relates to the use of such antibodies for passive immunization, preferably of humans, and to the use of such antibodies for the treatment of nicotine addiction in humans.

RELATED ART

Bjercke et al. 1986 (J Immunol Methods, Vol. 90(2) pp. 203-13) disclose stereospecific monoclonal antibodies against (S)-(−)-nicotine. The monoclonal anti-nicotine antibodies of Bjercke et al. 1986 were produced by the hybridoma technology and were, thus, derived from mouse cells. Bjercke et al. 1986 further describe the use of such monoclonal antibodies in the development of ELISA based assays for nicotine.

Isomura et al. 2001 (J. Org. Chem. Vol. 66 pp. 4115-4121) describe the preparation of haptens for the generation of antibodies specific for naturally occurring (S)-nicotine, (S)- and (R)-nornicotine, and the metabolite (S)-cotinine with high optical purity. The authors report preliminary data for antinicotine antibodies, including monoclonal antibodies. The monoclonal antibodies of Isomura et al. 2001 were obtained from mice and exhibit Kd values for nicotine binding of $1.6 \times 10^{-7}$ M to $3.4 \times 10^{-7}$ M.

Keyler et al. 2005 (Drug Metab Dispos, Vol. 33(7) pp. 1056-61) describe the passive immunization of rats with monoclonal antibodies against nicotine. The authors found, inter alia, a reduced distribution of nicotine to the brain upon passive immunization. Also the monoclonal antibodies of Keyler et al. 2005 were produced by hybridoma technology.

Pentel et al. 2006 (J Pharmacol Exp Ther, Vol. 317(2) pp. 660-6) studied inter alia the passive immunization of rats with the monoclonal antibody Nic311, an antibody described by Kepler et al. 2005, and hereby in particular the differential effects of passive immunization with this antibody on the acute and chronic distribution of nicotine to the brain. It has been suggested in the prior art that passive immunization of humans with nicotine specific antibodies may be useful in the treatment of nicotine addiction and may be supportive during smoking cessation. However, with respect to Nic311 Pentel et al. 2006 further conclude that a therapeutic monoclonal antibody would need to be humanized to reduce its own immunogenicity for clinical use.

The monoclonal antibodies against nicotine which are known from the prior art are derived from non-human sources and are therefore therapeutically not useful due to their strong immunogenicity in humans and due to safety concerns resulting thereof.

SUMMARY OF THE INVENTION

The invention provides human monoclonal antibodies that are specifically binding nicotine, wherein preferably said monoclonal antibodies are fully human antibodies. Typically and preferably, the monoclonal antibodies disclosed herein are not immunogenic in humans and are therefore suitable for the passive immunization of humans. Furthermore, it has surprisingly been found that monoclonal antibodies of the invention are specifically binding (S)-(−)-nicotine and (R)-(+)-nicotine. Like (S)-(−)-nicotine also the (R)-(+)-stereoisomer of nicotine is present in the tobacco plant. In addition, it can be formed by the combustion process during smoking and has qualitatively similar activities on the central nervous system as (S)-(−)-nicotine (Hukkanen J. et al., 2005, Pharmacol. Rev. 57, 79-115).

The monoclonal antibodies of the invention were cloned following a procedure disclosed in PCT/EP2007/061570: (1) nicotine-specific B-cells of a human subject were selected; (2) VH and VL regions of these cells were cloned into an alphaviral library; (3) a cells surface display of scFv antibodies was performed on mammalian cells; (4) cells displaying nicotine specific scFv antibodies were selected; (5) VH and VL regions of these scFv antibodies were cloned; and (6) monoclonal antibodies specifically binding nicotine were expressed in different formats, e.g. as scFv-Fc-fusion or as human IgG2, preferably as fully human IgG2. Applying this procedure, seven independent antibody clones were obtained which, when expressed as scFv-Fc fusion or IgG2, bound nicotine with a Kd value in the nanomolar or low nanomolar range.

Thus, in one aspect, the invention relates to a monoclonal antibody specifically binding nicotine, wherein said monoclonal antibody is a human monoclonal antibody and wherein preferably said human monoclonal antibody is a fully human monoclonal antibody.

These clones were sequenced and human CDRs conferring specificity to nicotine were identified. It has surprisingly been found that several of these antibodies share the same CDRs in different combinations (see Table 1).

TABLE 1

SEQ ID NOs of CDR sequences of nicotine-specific human antibodies.

| mAb | VH Chain | | | VL Chain | | |
|---|---|---|---|---|---|---|
| | CDR 1 | CDR 2 | CDR 3 | CDR 1 | CDR 2 | CDR 3 |
| F018 | 1 | 2 | 3 | 5 | 8 | 9 |
| F063 | 1 | 2 | 4 | 6 | 8 | 10 |
| J004 | 1 | 2 | 4 | 7 | 8 | 10 |
| J042 | 1 | 2 | 4 | 5 | 8 | 10 |
| N049 | 1 | 2 | 4 | 6 | 8 | 10 |
| I022 | 11 | 12 | 13 | 14 | 15 | 16 |
| N038 | 17 | 18 | 19 | 20 | 21 | 22 |

In a further aspect, the invention relates to a monoclonal antibody specifically binding nicotine, wherein preferably said monoclonal antibody is a human monoclonal antibody, and wherein said monoclonal antibody comprises at least one heavy chain variable region (HCVR), wherein said HCVR comprises: (a) one HC CDR1, wherein said HC CDR1 comprises or preferably consists of the peptide of any one of SEQ ID NOs 1, 11 and 17, and wherein preferably said HC CDR1 is located at CDR1 position within the framework of said HCVR; (b) one HC CDR2, wherein said HC CDR2 comprises or preferably consists of the peptide of any one of SEQ ID NOs 2, 12, and 18, and wherein preferably said HC CDR2 is located at CDR2 position within the framework of said HCVR; and/or (c) one HC CDR3, wherein said HC CDR3 comprises or preferably consists of the peptide of any one of SEQ ID NOs 3, 4, 13 and 19, and wherein preferably said HC CDR3 is located at CDR3 position within the framework of said HCVR.

In a further aspect, the invention relates to a monoclonal antibody specifically binding nicotine, wherein preferably said monoclonal antibody is a human monoclonal antibody, wherein said monoclonal antibody comprises at least one light chain variable region (LCVR), wherein said LCVR comprises (a) one LC CDR1, wherein said LC CDR1 comprises or preferably consists of the peptide of any one of SEQ ID NOs 5, 6, 7, 14 and 20; and wherein preferably said LC CDR1 is located at CDR1 position within the framework of said LCVR; (b) one LC CDR2, wherein said LC CDR2 comprises or preferably consists of the peptide of any one of SEQ ID NOs 8, 15 and 21, and wherein preferably said LC CDR2 is located at CDR2 position within the framework of said LCVR; and/or (c) one LC CDR3, wherein said LC CDR3 comprises or preferably consists of the peptide of any one of SEQ ID NOs 9, 10, 16 and 22, and wherein preferably said LC CDR3 is located at CDR3 position within the framework of said LCVR.

In a further aspect, the invention relates to a monoclonal antibody specifically binding nicotine, wherein preferably said monoclonal antibody is a human monoclonal antibody, and wherein said monoclonal antibody comprises at least one HCVR, wherein said HCVR comprises: (a) one HC CDR1, wherein said HC CDR1 comprises or preferably consists of the peptide of any one of SEQ ID NOs 1, 11 and 17, and wherein preferably said HC CDR1 is located at CDR1 position within the framework of said HCVR; (b) one HC CDR2, wherein said HC CDR2 comprises or preferably consists of the peptide of any one of SEQ ID NOs 2, 12, and 18, and wherein preferably said HC CDR2 is located at CDR2 position within the framework of said HCVR; and/or (c) one HC CDR3, wherein said HC CDR3 comprises or preferably consists of the peptide of any one of SEQ ID NOs 3, 4, 13 and 19, and wherein preferably said HC CDR3 is located at CDR3 position within the framework of said HCVR; and/or, preferably and, wherein said monoclonal antibody comprises at least one LCVR, wherein said LCVR comprises: (a) one LC CDR1, wherein said LC CDR1 comprises or preferably consists of the peptide of any one of SEQ ID NOs 5, 6, 7, 14 and 20; and wherein preferably said LC CDR1 is located at CDR1 position within the framework of said LCVR; (b) one LC CDR2, wherein said LC CDR2 comprises or preferably consists of the peptide of any one of SEQ ID NOs 8, 15 and 21, and wherein preferably said LC CDR2 is located at CDR2 position within the framework of said LCVR; and/or (c) one LC CDR3, wherein said LC CDR3 comprises or preferably consists of the peptide of any one of SEQ ID NOs 9, 10, 16 and 22, and wherein preferably said LC CDR3 is located at CDR3 position within the framework of said LCVR.

Typically and preferably, said monoclonal antibody is recombinantly produced. The monoclonal antibodies of the invention can be expressed in any naturally occurring or synthetic format. In a preferred embodiment said monoclonal antibody is an IgG, preferably an IgG2.

In a further aspect, the invention relates to a HCVR of a monoclonal antibody, wherein said monoclonal antibody is a human monoclonal antibody, and wherein said monoclonal antibody is specifically binding (S)-(−)-nicotine and (R)-(+)-nicotine, and wherein said HCVR comprises: (a) one HC CDR1, wherein said HC CDR1 consists of the peptide of SEQ ID NO:1; (b) one HC CDR2, wherein said HC CDR2 consists of the peptide of SEQ ID NO:2; and (c) one HC CDR3, wherein said HC CDR3 consists of the peptide of any one of SEQ ID NOs 3 and 4.

In a further aspect, the invention relates to a LCVR of a monoclonal antibody, wherein said monoclonal antibody is a human monoclonal antibody, and wherein said monoclonal antibody is specifically binding (S)-(−)-nicotine and (R)-(+)-nicotine, and wherein said LCVR comprises: (a) one LC CDR1, wherein said LC CDR1 consists of the peptide of any one of SEQ ID NOs 5, 6, and 7; (b) one LC CDR2, wherein said LC CDR2 consists of the peptide of SEQ ID NO:8; (c) one LC CDR3, wherein said LC CDR3 consists of the peptide of any one of SEQ ID NOs 9 and 10.

In a further aspect, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 1 to 100 nM; and wherein the dissociation constant Kd of said binding of said monoclonal antibody to said (R)-(+)-nicotine is 1 to 100 nM. In a preferred embodiment, said monoclonal antibody is binding (S)-(−)-nicotine and (R)-(+)-nicotine, wherein the dissociation constant Kd of said binding of said monoclonal antibody to said (S)-(−)-nicotine is 1 to 70 nM, preferably 1 to 40 nM, and further preferably 1 to 10 nM, wherein further preferably Kd is determined using said monoclonal antibody in the IgG2 format; and wherein the dissociation constant Kd of said binding of said monoclonal antibody to said (R)-(+)-nicotine is 1 to 70 nM, preferably 1 to 50 nM, further preferably 1 to 40 nM, again further preferably 1 to 20 nM, and still further preferably 1 to 10 nM, wherein further preferably Kd is determined using said monoclonal antibody in the IgG2 format. In a very preferred embodiment said monoclonal antibody is binding (S)-(−)-nicotine and (R)-(+)-nicotine, wherein the dissociation constant Kd of said binding of said monoclonal antibody to said (S)-(−)-nicotine is 1 to 70 nM, preferably 1 to 40 nM, and further preferably 1 to 10 nM, wherein further preferably Kd is determined using said monoclonal antibody in the IgG2 format; and wherein the dissociation constant Kd of said binding of said monoclonal antibody to said (R)-(+)-nicotine is 1 to 20 nM, and further preferably 1 to 10 nM, wherein further preferably Kd is determined using said monoclonal antibody in the IgG2 format. In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is 1 to 10 nM, wherein further preferably Kd is determined using said monoclonal antibody in the IgG2 format; and wherein the dissociation constant Kd of said binding of said monoclonal antibody to said (R)-(+)-nicotine is 1 to 10 nM, wherein further preferably Kd is determined using said monoclonal antibody in the IgG2 format. Preferably, said monoclonal antibody is a human monoclonal antibody, wherein said monoclonal antibody comprises at least one HCVR, wherein said HCVR comprises: (a) one HC CDR1, wherein said HC CDR1 comprises or preferably consists of the peptide of any one of SEQ ID NOs 1, 11 and 17, very preferably consists of the peptide of SEQ ID NO:1, and wherein preferably said HC CDR1 is located at CDR1 position within the framework of said HCVR; (b) one HC CDR2, wherein said HC CDR2 comprises or preferably consists of the peptide of any one of SEQ ID NOs 2, 12, and 18, very preferably consists of the peptide of SEQ ID NO:2, and wherein preferably said HC CDR2 is located at CDR2 position within the framework of said HCVR; and/or (c) one HC CDR3, wherein said HC CDR3 comprises or preferably consists of the peptide of any one of SEQ ID NOs 3, 4, 13 and 19, very preferably consists of the peptide of SEQ ID NO:3, and wherein preferably said HC CDR3 is located at CDR3 position within the framework of said HCVR; and/or, preferably and, wherein said monoclonal antibody comprises at least one LCVR, wherein said LCVR comprises: (a) one LC CDR1, wherein said LC CDR1 comprises or preferably consists of the peptide of any one of SEQ ID NOs 5, 6, 7, 14 and 20; very preferably consists of the peptide of SEQ ID NO:5, and wherein preferably said LC CDR1 is located at CDR1 position within the framework of said LCVR; (b) one LC CDR2, wherein said LC CDR2 comprises or preferably consists of the peptide of any one of SEQ ID NOs 8, 15 and 21, very preferably consists of the peptide of SEQ ID NO:8, and wherein preferably said LC CDR2 is located at CDR2 position within the framework of said LCVR; and/or (c) one LC CDR3, wherein said LC CDR3 comprises or preferably consists of the peptide of any one of SEQ ID NOs 9, 10, 16 and 22, very preferably consists of the peptide of SEQ ID NO:9, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 1 to 10 nM; and wherein the dissociation constant Kd of said binding of said monoclonal antibody to said (R)-(+)-nicotine is 1 to 10 nM, wherein preferably Kd is determined using said monoclonal antibody in the IgG2 format; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:3, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:9, and wherein preferably said LC CDR3 is located at CDR3 position within the framework of said LCVR, and wherein preferably position 7 to 117 of said HCVR consist of the peptide of SEQ ID NO:24, and wherein position 5 to 107 of said LCVR consist of the peptide of SEQ ID NO:26.

In a further aspect, the invention relates a nucleic acid molecule encoding a variable region or the invention, a monoclonal antibody of the invention or an individual chain thereof.

In a further aspect, the invention relates to an expression vector comprising at least one nucleic acid molecule of the invention. In a further aspect, the invention relates to a host cell comprising at least one nucleic acid molecule of the invention or at least one expression vector of the invention.

The monoclonal antibody of the invention is useful for passive immunization, preferably of humans and in the treatment of nicotine addiction. Thus, in a further aspect the invention relates to a pharmaceutical composition comprising at least one monoclonal antibody of the invention.

In a further aspect, the invention relates to a method of passive immunization, said method comprising administering to a subject an effective amount of the monoclonal antibody of the invention or an effective amount of the pharmaceutical composition of the invention.

In a further aspect, the invention relates to a method of treating nicotine addiction, said method comprising administering to a subject an effective amount of the monoclonal antibody of the invention or an effective amount of the pharmaceutical composition of the invention.

In a further aspect, the invention relates to a monoclonal antibody of the invention or a pharmaceutical composition of the invention, for use in passive immunization, preferably in a human.

In a further aspect, the invention relates to a monoclonal antibody of the invention or to the pharmaceutical composition of the invention, for use in the treatment of nicotine addiction, preferably in a human.

In a further aspect, the invention relates to the use of the monoclonal antibody of the invention in the manufacture of a medicament for passive immunization, preferably against nicotine.

In a further aspect, the invention relates to the use of the monoclonal antibody of the invention in the manufacture of a medicament for the treatment of nicotine addiction, preferably in a human.

A further aspect of the invention is the use of an antibody of the invention in a method of quantitative and/or qualitative detection of nicotine, preferably in a blood sample and most preferably by ELISA.

It is to be understood that all embodiments and technical features disclosed herein relate to all aspects of the invention, and in any possible combination.

DESCRIPTION OF THE FIGURES

FIG. 1. Specificity of IgG2-F018. The binding of tritium-labeled (−)-nicotine (56 nM) to IgG2-F018 (50 nM) was measured by equilibrium dialysis in the presence of increasing concentrations of unlabeled (−)-nicotine, (−)-cotinine or acetylcholine. Averages of two independent experiments are given with standard deviation.

DETAILED DESCRIPTION OF THE INVENTION

"Antibody": As used herein, the term "antibody" refers to a molecule, preferably a protein, which is capable of specifically binding an antigen, typically and preferably by binding an epitope or antigenic determinant of said antigen, or a hapten. Preferably, the term antibody refers to an antigen or hapten binding molecule comprising at least one variable region, wherein preferably said molecule comprises least one HCVR and/or at least one LCVR. Further preferably, the term antibody refers to an antigen or hapten binding molecule comprising at least one, preferably exactly two antigen binding sites, wherein each of said antigen binding site(s) is formed by one HCVR and one LCVR. Furthermore, the term antibody refers to whole antibodies, preferably of the IgG, IgA, IgE, IgM, or IgD class, more preferably of the IgG class, most preferably IgG1, IgG2, IgG3, and IgG4, and to antigen binding fragments thereof. In a preferred embodiment said whole antibodies comprise either a kappa or a lambda light chain. The term "antibody" also refers to antigen or hapten binding antibody fragments, preferably to proteolytic fragments and their recombinant analogues. most preferably to Fab, Fab' and F(ab')2, and Fv. The term antibody further encompasses a protein comprising at least one, preferably two variable regions, wherein further preferably said protein comprises exactly one HCVR and exactly one LCVR. In a preferred embodiment the term antibody refers to a single chain antibody, preferably to scFv. Thus, preferred antibodies are single chain antibodies, preferably scFvs, disulfide-linked Fvs (sdFv) and fragments comprising either a light chain variable region (LCVR) or a heavy chain variable region (HCVR). In the context of the invention the term "antibody" preferably refers to recombinant antibodies, including recombinant proteins consisting of a single polypeptide, wherein said polypeptide comprises at least one, preferably exactly one, variable region. In the context of the invention recombinant antibodies may further comprise functional elements, such as, for example, a linker region, a signal peptide or hydrophobic leader sequence, a detection tag and/or a purification tag (e.g. Fc).

"Fv": The term Fv refers to the smallest proteolytic fragment of an antibody capable of binding an antigen or hapten and to recombinant analogues of said fragment.

"single chain antibody": A single chain antibody is an antibody consisting of a single polypeptide. Preferred single chain antibodies consist of a polypeptide comprising at least one, preferably exactly one VR, wherein preferably said VR is a HCVR. More preferred single chain antibodies consist of a polypeptide comprising a at least one, preferably exactly one, HCVR and at least one, preferably exactly one, LCVR. Still more preferred single chain antibodies comprise exactly one HCVR and exactly one LCVR. Most preferred single chain antibodies are scFv, wherein said scFv consist of a single polypeptide comprising exactly one HCVR and exactly one LCVR, wherein said HCVR and said LCVR are linked to each other by a linker region, wherein preferably said linker region consists of at least 15, preferably of 15 to 20 amino acids (Bird et al. (1988) Science, 242(4877):423-426). Further preferred single chain antibodies are scFv, wherein said scFv are encoded by a coding region, wherein said coding region, in 5' to 3' direction, comprises in the following order: (1) a light chain variable region (LCVR) consisting of light chain framework (LC FR) 1, complementary determining region (LC CDR) 1, LC FR2, LC CDR 2, LC FR3, LC CDR3 and LC FR4 from a κ or λ light chain; (2) a flexible linker (L), and (3) a heavy chain variable region (HCVR) consisting of framework (HC FR) 1, complementary determining region (HC CDR) 1, HC FR2, HC CDR2, HC FR3, HC CDR3 and HC FR4. Alternatively, single chain antibodies are scFv, wherein said scFv are encoded by a coding region, wherein said coding region, in 5' to 3' direction, comprises in the following order: (1) a heavy chain variable region (HCVR) consisting of framework (HC FR) 1, complementary determining region (HC CDR) 1, HC FR2, HC CDR2, HC FR3, HC CDR3 and HC FR4; (2) a flexible linker (L), and (3) a light chain variable region (LCVR) consisting of light chain framework (LC FR) 1, complementary determining region (LC CDR) 1, LC FR2, LC CDR2, LC FR3, LC DR3 and LC FR4 from a κ or λ light chain.

"diabody": The term "diabody" refers to an antibody comprising two polypeptide chains, preferably two identical polypeptide chains, wherein each polypeptide chain comprises a HCVR and a LCVR, wherein said HCVR and said LCVR are linked to each other by a linker region, wherein preferably said linker region comprises at most 10 amino acids (Huston et al. (1988), PNAS 85(16):587958-83; Holliger et al. (1993), PNAS 90(14):6444-6448, Hollinger & Hudson, 2005, Nature Biotechnology 23(9):1126-1136; Arndt et al. (2004) FEBS Letters 578(3):257-261). Preferred linker regions of diabodies comprise 0, 1, 2, 3, 4, 5, 6, 7, 8, 9, or 10 amino acids.

"human antibody": As used herein, the term "human antibody" refers to an antibody, preferably a recombinant antibody, essentially having the amino acid sequence of a human immunoglobulin, or a fragment thereof, and includes antibodies isolated from human immunoglobulin libraries. In the context of the invention "human antibodies" may comprise a limited number of amino acid exchanges as compared to the sequence of a native human antibody. Such amino acid exchanges can, for example, be caused by cloning procedures. However, the number of such amino acid exchanges in human antibodies of the invention is preferably minimized. Preferably, the amino acid sequence of human antibodies is at least 85%, preferably 90%, more preferably 95%, even more preferably at least 96%, still more preferably 97%, again still more preferably 98%, again still more preferably 99% and most preferably 100% identical to that of native human antibodies. More preferably, the amino acid sequence of human antibodies is at least 85%, preferably 90%, more preferably 95%, even more preferably at least 96%, still more preferably 97%, again still more preferably 98%, again still more preferably 99% and most preferably 100% identical to that of native human antibodies which are specifically binding to the antigen or hapten of interest. Most preferably, the amino acid sequence of human antibodies is at least 85%, preferably 90%, more preferably 95%, even more preferably at least 96%, still more preferably 97%, again still more preferably 98%, again still more preferably 99% and most preferably 100% identical to that of native human antibodies which are specifically binding to nicotine, preferably to (S)-(−)-nicotine and/or to (R)-(+)-nicotine.

Preferred recombinant human antibodies differ from native human antibodies in at most 20, 15, 10, 9, 8, 7, 6, 5, 4, 3, 2, or 1 amino acid. Very preferably, differences in the amino acid sequence of recombinant human antibodies and native human antibodies are eliminated my means of molecular cloning, and thus, most preferably, the amino acid sequence of a recombinant human antibodies and native human antibodies are identical. Such antibodies are also referred to as "fully human antibodies". An illustrative example how a fully human antibody may be obtained from a human antibody selected from a human antibody library is provided in Example 6. Typically and preferably, fully human antibodies are not immunogenic in humans.

Preferred human antibodies comprise (a) least one, preferably one, HCVR, (b) at least one, preferably one, HCCR, (c) at least one, preferably one, LCVR, and (d) at least one, preferably one, LCCR, wherein said at least one HCVR, and/or said at least one HCCR, and/or said at least one LCVR, and/or said at least one LCCR are at least 85%, preferably 90%, more preferably 95%, still more preferably at least 96%, again still more preferably 97%, again still more preferably 98%, again still more preferably 99%, and most preferably 100% identical to the respective native human regions.

It is well established that the constant regions of immunoglobulins, including human immunoglobulins, exist in various allotypes, i.e. that the amino acid sequence of said constant regions may differ to a certain extend between individuals of a population. Allotypes of the constant regions of human immunoglobulins are very well studied and the sequence information is readily available to the artisan from various sources, including the Immuno Genetics Information System (http://imgt.cines.fr/). It is to be understood that different allotypes of the constant regions of one immunoglobulin are interchangeable for the purpose of the invention. For example, the gamma 2 heavy chain of a monoclonal antibody of the invention may comprise any existing allotype of a human gamma 2 HCCR.

"monoclonal antibody": As used herein, the term "monoclonal antibody" refers to an antibody population comprising only one single antibody species, i.e. antibodies having an identical amino acid sequence.

"constant region (CR)": The term "constant region" refers to a light chain constant region (LCCR) or a heavy chain constant region (HCCR) of an antibody. Typically and preferably, said CR comprises one to four immunoglobulin domains characterized by disulfide stabilized loop structures. Preferred CRs are CRs of immunoglobulins, preferably of human immunoglobulins, wherein further preferably said immunoglobulins, preferably said human immunoglobulins are selected from the group consisting of IgG1, IgG2, IgG3, IgG4, IgA, IgE, IgM, and IgD. Very preferred CRs are human CRs comprising or consisting of an amino acid sequence available from public databases, including, for example the Immuno genetic Information System (http://imgt.cines.fr/).

light chain constant region (LCCR): The LCCR, more specifically the kappa LCCR or the lambda LCCR, typically represents the C-terminal half of a native kappa or lambda light chain of an native antibody. A LCCR typically comprises about 110 amino acids representing one immunoglobulin domain.

heavy chain constant region (HCCR): The constant region of a heavy chain comprises about three quarters or more of the heavy chain of an antibody and is situated at its C-terminus. Typically the HCCR comprises either three or four immunoglobulin domains. Preferred HCCRs are selected from gamma HCCR, alpha HCCR, epsilon HCCR, my HCCR, and delta HCCR. Very preferred are gamma HCCR, wherein preferably said gamma HCCR is selected from gamma 1 HCCR, gamma 2 HCCR, gamma 3 HCCR, and gamma 4 HCCR, wherein most preferably said gamma HCCR is a gamma 2 HCCR.

"variable region (VR)": Refers to the variable region or variable domain of an antibody, more specifically to the heavy chain variable region (HCVR) or to the light chain variable region (LCVR). Typically and preferably, a VR comprises a single immunoglobulin domain. Preferred VRs are VRs of immunoglobulins, preferably of human immunoglobulins, wherein further preferably said immunoglobulins, preferably said human immunoglobulins, are selected from the group consisting of IgG1, IgG2, IgG3, IgG4, IgA, IgE, IgM, and IgD. VRs of various species are known in the art. Preferred VRs are human VRs, wherein the framework of said human VRs exhibit at least 80%, preferably at least 85%, more preferably 90%, again more preferably at least 95%, most preferably at least 99% sequence identity with the framework of any known human VR sequence. Preferred VRs are human VRs, wherein the framework of said human VRs exhibit at least 80%, preferably at least 85%, more preferably 90%, again more preferably at least 95%, most preferably at least 99% sequence identity with the framework of any human VR sequence available from public databases, most preferably with any human VR sequence available from the Immunogenetics Information System (http://imgt.cines.fr/).

Each VR comprises so called complementarity determining regions (CDRs) which are determining the binding characteristics of the antibody and which are embedded in the so called framework. Typically and preferably, VRs comprise three CDRs, preferably CDR1, CDR2, and CDR3, which are embedded into the framework (FR 1-4). Thus, in a preferred embodiment, a VR comprises the following elements in the following order from the N- to the C-terminus: FR1-CDR1-FR2-CDR2-FR3-CDR3-FR4.

Generally VRs comprise or preferably consist of a polypeptide, wherein said polypeptide is a product of a member of a family of V-gene segments in combination with further gene segments as, for example, D and J gene segments (HCVR) or J gene segments (LCDR).

"light chain variable region (LCVR)": Light chain variable regions are encoded by rearranged nucleic acid molecules and are either a kappa LCVR or a lambda LCVR. Human kappa LCVRs comprise a polypeptide, wherein said polypeptide is a product of a member of family 1 to 7 of human kappa V-gene segments. In the context of the invention preferred kappa LCVRs are human kappa LCVRs, preferably human kappa LCVRs which are encoded by a DNA which can be amplified from human B cells using a primer combination of any one of the oligonucleotides disclosed as SEQ ID NO:49 to 52 of PCT/EP2007/061570 with any one oligonucleotide disclosed as SEQ ID NO:53 to 56 of PCT/EP2007/061570, and further preferably, PCR conditions described in Example 3 or of PCT/EP2007/061570.

Human lambda LCVRs comprise a polypeptide, wherein said polypeptide is a product of a member of family 1 to 11 of human lambda V-gene segments. In the context of the invention preferred lambda LCVRs are human lambda LCVRs, preferably human lambda LCVRs which are encoded by a DNA which can be amplified from human B cells using a primer combination of any one of SEQ ID NO:57 to 65 of PCT/EP2007/061570 with any one of SEQ ID NO:66 to 68 of PCT/EP2007/061570, and further preferably, PCR conditions described in Example 3 of PCT/EP2007/061570.

Typically and preferably, LCVRs comprise three LC CDRs, preferably LC CDR1, LC CDR2, and LC CDR3, which are embedded into the light chain framework (LC FR 1-4). Thus, in a preferred embodiment, a LCVR comprises the following elements in the following order from the N- to the C-terminus: LC FR1-LC CDR1-LC FR2-LC CDR2-LC FR3-LC CDR3-LC FR4.

"heavy chain variable region (HCVR)": Heavy chain variable regions are encoded by rearranged nucleic acid molecules. Human HCVRs comprise a polypeptide, wherein said polypeptide is a product of a member of family 1 to 7 of human lambda V-gene segments. In the context of the invention preferred HCVRs are human HCVRs, preferably human HCVRs which are encoded by a DNA which can be amplified from human B cells using a primer combination of any one of SEQ ID NO:42 to 47 of PCT/EP2007/061570 with SEQ ID NO:48 of c PCT/EP2007/061570 and, further preferably, PCR conditions described in Example 3 of PCT/EP2007/061570.

Typically and preferably, HCVRs comprise three HC CDRs, preferably HC CDR1, HC CDR2, and HC CDR3, which are embedded into the heavy chain framework (HC FR 1-4). Thus, in a preferred embodiment, a HCVR comprises the following elements in the following order from the N- to the C-terminus: HC FR1-HC CDR1-HC FR2-HC CDR2-HC FR3-HC CDR3-HC FR4.

"CDR": The complementarity determining region (CDR) 1, 2 and 3 of the HCVR and of the LCVR, respectively, of an antibody can be identified by methods generally known in the art. For the purpose of this application, CDR and FR boundaries are defined as set forth by Scavinger et al. 1999 (Exp Clin Immunogenet., Vol. 16 pp. 234-240), or by Lefranc et al. 2003 (Developmental and Comparative Immunology Vol. 27 pp. 55-77).

"antigen": As used herein, the term "antigen" refers to a molecule which is bound by an antibody. An antigen is recognized by the immune system and/or by a humoral immune response and can have one or more epitopes, preferably B-cell epitopes, or antigenic determinants.

"hapten": The term "hapten" generally refers to an chemical compound, wherein said compound is not capable of inducing an immune response in an animal by itself, but wherein said compound will be capable of inducing an immune response in an animal when said compound is bound to a carrier, preferably to a carrier protein. In the context of the invention, "hapten" refers to nicotine.

"nicotine": The term "nicotine" as used herein preferably refers to (S)-(−)-nicotine or (R)-(+) nicotine, or any mixture thereof. Most preferably, nicotine refers to (S)-(−)-nicotine.

"specifically binding": The specificity of an antibody relates to the antibody's capability of specifically binding an antigen or hapten. The specificity of this interaction between the antibody and the antigen/hapten (affinity) is characterized by a binding constant or, inversely, by a dissociation constant (Kd). It is to be understood that the apparent affinity of an antibody to an antigen/hapten in a multivalent interaction depends on the structure of the antibody and of the antigen/hapten, and on the actual assay conditions. The apparent affinity of an antibody to an antigen/hapten in a multivalent interaction may be significantly higher than in a monovalent interaction due to avidity. Thus, affinity is preferably determined under conditions favoring monovalent interactions. Kd can be determined by methods known in the art. Kd of a given combination of antibody and antigen/hapten is preferably determined by ELISA, wherein a constant amount of immobilized antigen/hapten is contacted with a serial dilution of a known concentration of a purified antibody, preferably a monovalent antibody, for example scFv or Fab fragment. Kd is then determined as the concentration of the antibody where half-maximal binding is observed. In a preferred embodiment Kd is determined by equilibrium dialysis, preferably under conditions as described in Example 7. Alternatively, Kd of a monovalent interaction of an antibody and an antigen/hapten is determined by Biacore analysis as the ratio of on rate ($k_{on}$) and off rate ($k_{off}$). Lower values of Kd indicate a more specific binding of the antibody to the antigen/hapten than higher values. In the context of the application, an antibody is considered to be "specifically binding an antigen/hapten", when the dissociation constant (Kd), preferably determined as described above, and further preferably determined in a monovalent interaction, is at most 1 mM ($<=10^{-3}$ M), preferably at most 1 μM ($<=10^{-6}$ M), most preferably at most 1 nM ($<=10^{-9}$ M). Very preferred are antibodies capable of binding an antigen/hapten with a Kd of less than 100 nM ("low nanomolar range"), wherein further preferably Kd is determined in a monovalent interaction. Further preferred antibodies are capable of binding an antigen/hapten with a Kd of 1 to 1000 nM, more preferably of 5 to 800 nM, still more preferably of 5 to 90 nM, most preferably of 5 to 50 nM, wherein further preferably Kd is determined in a monovalent interaction.

"equal": In the context of the application the values of two dissociation constants (Kd) of a monoclonal antibody and a substance are regarded as being "equal" when said values differ by a factor of at most 10, preferably at most 9, more preferably at most 8, still more preferably at most 7, still more preferably at most 6, still more preferably at most 5, still more preferably at most 4, still more preferably at most 3, still more preferably at most 2, and most preferably at most 1.5. In a very preferred embodiment two Kd values are regarded as being equal when they differ by a factor of less than 5.

"effective amount": A therapeutically effective amount of a monoclonal antibody of the invention or of a pharmaceutical composition of the invention generally refers to an amount necessary to achieve, at dosages and periods of time necessary, the desired therapeutic result, wherein preferably said result is preventing, reducing or slowing down the nicotine entry into the brain, preferably in a human, and/or, ultimately, smoking cessation. With respect to a therapeutic treatment of a human, an "effective amount" typically refers to an amount of 1 mg to 1000 mg, preferably 10 mg to 500 mg, more preferably 10 mg to 300 mg, still more preferably 50 mg to 200 mg, and most preferably about 100 mg of said monoclonal antibody.

"Tag": The term tag, preferably a purification or detection tag, refers to a polypeptide segment that can be attached to a second polypeptide to provide for purification or detection of the second polypeptide or provides sites for attachment of the second polypeptide to a substrate. In principle, any peptide or protein for which an antibody or other specific binding agent is available can be used as an affinity tag. Tags include haemagglutinin tag, myc tag, poly-histidine tag, protein A, glutathione S transferase, Glu-Glu affinity tag, substance P, FLAG peptide, streptavidin binding peptide, or other antigenic epitope or binding domain (mostly taken from U.S. 06/686,168).

A library-based screening method for the identification, isolation and cloning of scFv specifically binding an antigen or hapten of interest is disclosed in PCT/EP2007/061570. In particular, said method allows for the identification, isolation and cloning of human scFv and for the subsequent generation of fully human antibodies, including Fab fragments and whole IgG. Applying said technology, human monoclonal antibodies specifically binding nicotine have been identified and cloned.

In one aspect, the invention provides a monoclonal antibody specifically binding nicotine, wherein said monoclonal antibody is a human monoclonal antibody, wherein preferably said nicotine is selected from (S)-(−)-nicotine and (R)-(+)-nicotine, and wherein most preferably said nicotine is (S)-(−)-nicotine; and wherein further preferably said human monoclonal antibody is a fully human monoclonal antibody.

In a preferred embodiment said monoclonal antibody is specifically binding (S)-(−)-nicotine and (R)-(+)-nicotine.

In one embodiment said monoclonal antibody is binding nicotine, preferably (S)-(−)-nicotine, with a dissociation constant Kd of 1 to 1000 nM, more preferably of 1 to 800 nM, still more preferably of 1 to 100 nM, most preferably of 5 to 90 nM, wherein further preferably Kd is determined using said monoclonal antibody in the IgG2 format. In a further preferred embodiment Kd is determined in a monovalent interaction, most preferably in an assay essentially as described in Example 7.

In a further preferred embodiment said monoclonal antibody is binding (S)-(−)-nicotine and (R)-(+)-nicotine, wherein the dissociation constant Kd of said binding of said monoclonal antibody to said (S)-(−)-nicotine is 1 to 100 nM; and wherein the dissociation constant Kd of said binding of said monoclonal antibody to said (R)-(+)-nicotine is 1 to 100 nM.

In a more preferred embodiment said monoclonal antibody is binding (S)-(−)-nicotine and (R)-(+)-nicotine, wherein the dissociation constant Kd of said binding of said monoclonal antibody to said (S)-(−)-nicotine is 0.1 to 100 nM, preferably 0.1 to 70 nM, further preferably 0.1 to 50 nM, again further preferably 0.1 to 40 nM, again further preferably 0.1 to 20 nM, and further preferably 0.1 to 10 nM, and further preferably 1 to 10 nM, wherein further preferably Kd is determined using said monoclonal antibody in the IgG2 format; and wherein the dissociation constant Kd of said binding of said monoclonal antibody to said (R)-(+)-nicotine is 0.1 to 100 nM, preferably 0.1 to 70 nM, further preferably 0.1 to 50 nM, again further preferably 0.1 to 40 nM, again further preferably 0.1 to 20 nM, and again further preferably 0.1 to 10 nM, and still further preferably 1 to 10 nM, wherein further preferably Kd is determined using said monoclonal antibody in the IgG2 format. In a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is 0.1 to 40 nM, and further preferably 0.1 to 10 nM, and still further preferably 1 to 10 nM, wherein further preferably Kd is determined using said monoclonal antibody in the IgG2 format; and wherein the dissociation constant Kd of said binding of said monoclonal antibody to said (R)-(+)-nicotine is 0.1 to 50 nM, preferably 0.1 to 20 nM, and further preferably 0.1 to 10 nM, and still further preferably 1 to 10 nM, wherein further preferably Kd is determined using said monoclonal antibody in the IgG2 format. In again another very preferred embodiment said monoclonal antibody is binding (S)-(−)-nicotine and (R)-(+)-nicotine, wherein the dissociation constant Kd of said binding of said monoclonal antibody to said (S)-(−)-nicotine is 0.1 to 10 nM, preferably 1 to 10 nM, wherein preferably Kd is determined using said monoclonal antibody in the IgG2 format; and wherein the dissociation constant Kd of said binding of said monoclonal antibody to said (R)-(+)-nicotine is 0.1 to 10 nM, preferably 1 to 10 nM, wherein preferably Kd is determined using said monoclonal antibody in the IgG2 format.

In a further preferred embodiment said monoclonal antibody is binding (S)-(−)-nicotine and (R)-(+)-nicotine, wherein the dissociation constant Kd of said binding of said monoclonal antibody to said (S)-(−)-nicotine is 1 to 1000 nM, preferably 1 to 800 nM, still more preferably 1 to 100 nM, again further preferably 1 to 70 nM, again further preferably 1 to 50 nM, again further preferably 1 to 40 nM, again further preferably 1 to 20 nM, and still further preferably 1 to 10 nM, wherein further preferably Kd is determined using said monoclonal antibody in the IgG2 format; and wherein the dissociation constant Kd of said binding of said monoclonal antibody to said (R)-(+)-nicotine is 1 to 1000 nM, preferably 1 to 800 nM, still more preferably 1 to 100 nM, again further preferably 1 to 70 nM, again further preferably 1 to 50 nM, again further preferably 1 to 40 nM, again further preferably 1 to 20 nM, and still further preferably 1 to 10 nM, wherein further preferably Kd is determined using said monoclonal antibody in the IgG2 format. In a very preferred embodiment said monoclonal antibody is binding (S)-(−)-nicotine and (R)-(+)-nicotine, wherein the dissociation constant Kd of said binding of said monoclonal antibody to said (S)-(−)-nicotine is 1 to 100 nM, preferably 1 to 70 nM, again further preferably 1 to 40 nM, and further preferably 1 to 10 nM, wherein further preferably Kd is determined using said monoclonal antibody in the IgG2 format; and wherein the dissociation constant Kd of said binding of said monoclonal antibody to said (R)-(+)-nicotine is 1 to 100 nM, preferably 1 to 70 nM, again further preferably 1 to 50 nM, again further preferably 1 to 40 nM, again further preferably 1 to 20 nM, and further preferably 1 to 10 nM, wherein further preferably Kd is determined using said monoclonal antibody in the IgG2 format. In a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is 1 to 70 nM, preferably 1 to 40 nM, and further preferably 1 to 10 nM, wherein further preferably Kd is determined using said monoclonal antibody in the IgG2 format; and wherein the dissociation constant Kd of said binding of said monoclonal antibody to said (R)-(+)-nicotine is 1 to 50 nM, preferably 1 to 20 nM, and further preferably 1 to 10 nM, wherein further preferably Kd is determined using said monoclonal antibody in the IgG2 format. In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is 1 to 10 nM, wherein further preferably Kd is determined using said monoclonal antibody in the IgG2 format; and wherein the dissociation constant Kd of said binding of said monoclonal antibody to said (R)-(+)-nicotine is 1 to 10 nM, wherein further preferably Kd is determined using said monoclonal antibody in the IgG2 format.

In a further preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 100 nM, preferably lower than 70 nM, further preferably lower than 50 nM, again further preferably lower than 40 nM, again further preferably lower than 20 nM, and again further preferably lower than 10 nM, wherein further preferably Kd is determined using said monoclonal antibody in the IgG2 format; and wherein the dissociation constant Kd of said binding of said monoclonal antibody to said (R)-(+)-nicotine lower than 100 nM, preferably lower than 70 nM, further preferably lower than 50 nM, again further preferably lower than 40 nM, again further preferably lower than 20 nM, and again further preferably lower than 10 nM, wherein further preferably Kd is determined using said monoclonal antibody in the IgG2 format. In a very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 70 nM, preferably lower than 40 nM, and further preferably lower than 10 nM, wherein further preferably Kd is determined using said monoclonal antibody in the IgG2 format; and wherein the dissociation constant Kd of said binding of said monoclonal antibody to said (R)-(+)-nicotine is lower than 50 nM, preferably lower than 20 nM, and further preferably lower than 10 nM, wherein further preferably Kd is determined using said monoclonal antibody in the IgG2 format. In a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 10 nM, wherein further preferably Kd is determined using said monoclonal antibody in the IgG2 format; and wherein the dissociation constant Kd of said binding of said monoclonal antibody to said (R)-(+)-nicotine is lower than 20, preferably lower than 10 nM, wherein further preferably Kd is determined using said monoclonal antibody in the IgG2 format. In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 10 nM, wherein further preferably Kd is determined using said monoclonal antibody in the IgG2 format; and wherein the dissociation constant Kd of said binding of said monoclonal antibody to said (R)-(+)-nicotine is lower than 10 nM, wherein further preferably Kd is determined using said monoclonal antibody in the IgG2 format.

In a further preferred embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is equal to the dissociation constant Kd of said binding of said monoclonal antibody to said (R)-(+)-nicotine, wherein preferably Kd is determined using said monoclonal antibody in the IgG2 format.

In another preferred embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 2 to 5 times higher, preferably about 2 times higher, and most preferably 2 times higher than the dissociation constant Kd of said binding of said monoclonal antibody to said (R)-(+)-nicotine, wherein preferably Kd is determined using said monoclonal antibody in the IgG2 format.

In a further preferred embodiment said monoclonal antibody is capable of preventing, reducing or slowing down the nicotine entry into the brain, preferably in a human. In a further preferred embodiment said monoclonal antibody is capable of reducing the nicotine entry into the brain, preferably by at least 10%, 20%, 30%, 40%, 50% 60%, 70%, 80%, or 90% when assayed under conditions essentially as described in Example 8. Most preferably said monoclonal antibody is capable of reducing the nicotine entry into the brain, preferably by at least 60% when assayed under conditions essentially as described in Example 8.

In a further preferred embodiment said monoclonal antibody is capable of preventing, reducing or slowing down the nicotine entry into the brain of a subject, preferably of a human, when administered to said subject, preferably to said human, wherein preferably said monoclonal antibody is administered to said subject, preferably to said human, in an amount of 1 mg to 1000 mg, preferably 10 mg to 500 mg, more preferably 10 mg to 300 mg, still more preferably 50 mg to 200 mg, and most preferably about 100 mg.

The specificity of an antibody is mainly determined by the amino acid sequence of the complementarity determining regions (CDRs) in the heavy chain variable regions (HCVR) of said antibody and/or by the CDRs in the light chain variable regions (LCVR). The invention discloses CDRs of HCVRs (HC CDRs) and CDRs of the LCVRs (LC CDRs) of monoclonal antibodies, wherein said monoclonal antibodies are capable of specifically binding nicotine.

Thus, in a preferred embodiment said monoclonal antibody comprises at least one HCVR, wherein said HCVR comprises: (a) one HC CDR1, wherein said HC CDR1 comprises or preferably consists of the peptide of any one of SEQ ID NOs 1, 11 and 17, and wherein preferably said HC CDR1 is located at CDR1 position within the framework of said HCVR; (b) one HC CDR2, wherein said HC CDR2 comprises or preferably consists of the peptide of any one of SEQ ID NOs 2, 12, and 18, and wherein preferably said HC CDR2 is located at CDR2 position within the framework of said HCVR; and/or (c) one HC CDR3, wherein said HC CDR3 comprises or preferably consists of the peptide of any one of SEQ ID NOs 3, 4, 13 and 19, and wherein preferably said HC CDR3 is located at CDR3 position within the framework of said HCVR.

In a further preferred embodiment said monoclonal antibody comprises at least one LCVR, wherein said LCVR comprises: (a) one LC CDR1, wherein said LC CDR1 comprises or preferably consists of the peptide of any one of SEQ ID NOs 5, 6, 7, 14 and 20; and wherein preferably said LC CDR1 is located at CDR1 position within the framework of said LCVR; (b) one LC CDR2, wherein said LC CDR2 comprises or preferably consists of the peptide of any one of SEQ ID NOs 8, 15 and 21, and wherein preferably said LC CDR2 is located at CDR2 position within the framework of said LCVR; and/or (c) one LC CDR3, wherein said LC CDR3 comprises or preferably consists of the peptide of any one of SEQ ID NOs 9, 10, 16 and 22, and wherein preferably said LC CDR3 is located at CDR3 position within the framework of said LCVR.

It has surprisingly been found that some of the monoclonal antibodies which are capable of binding nicotine with a Kd in the nanomolar range, in particular F018, F063, J004, J042 and N049, share identical HC CDRs and/or LC CDRs in different combinations (cf. Table 1). Furthermore, it has surprisingly been found that heavy and light chain variable regions of antibodies F018, F063, J004, J042 and N049 are very closely related to one another and differed only at few amino acid positions.

Thus, in a very preferred embodiment (a) said HC CDR1 comprises or preferably consists of the peptide of SEQ ID NO:1; (b) said HC CDR2 comprises or preferably consists of the peptide of SEQ ID NO:2; and (c) said HC CDR3 comprises or preferably consists of the peptide of any one of SEQ ID NOs 3 and 4, wherein preferably (a) said LC CDR1 comprises or preferably consists of the peptide of any one of SEQ ID NOs 5, 6 and 7; (b) said LC CDR2 comprises or preferably consists of the peptide of SEQ ID NO:8; and (c) said LC CDR3 comprises or preferably consists of the peptide of any one of SEQ ID NOs 9 and 10.

In a preferred embodiment, said HCVR comprises a framework, wherein said framework is a product of a member of the VH family of V-gene segments, preferably of the VH4 family of V-gene segments, combined with a JH-gene segment.

In a very preferred embodiment (a) said HC CDR1 consists of the peptide of SEQ ID NO:1; (b) said HC CDR2 consists of the peptide of SEQ ID NO:2; and (c) said HC CDR3 consists of the peptide of SEQ ID NO:3.

In a further very preferred embodiment (a) said HC CDR1 consists of the peptide of SEQ ID NO:1; (b) said HC CDR2 consists of the peptide of SEQ ID NO:2; and (c) said HC CDR3 consists of the peptide of SEQ ID NO:4.

In one embodiment position 7 to 117 of said HCVR consists of the peptide of any one of SEQ ID NOs 24, 28, 33, and 39. In another embodiment position 7 to 117 of said HCVR is encoded by the nucleic acid of any one of SEQ ID NOs 23, 27, 32, 29, and 38.

The antibodies of the invention may differ from fully human antibodies in certain amino acid positions of the VRs due to cloning artifacts, wherein typically these positions are located near the N- and/or C-terminus of the variable region. Preferably, these artifacts are removed from the antibody in order to obtain fully human antibodies. A method for the generation of fully human monoclonal antibodies from antibodies still comprising said cloning artifacts is illustrated in Example 6. A similar approach is applied to all HCVRs and LCVRs disclosed herein. For example, in order to obtain fully human HCVRs, position 1 to 6 of the HCVRs of the invention is replaced by SEQ ID NO:50. Thus, in a preferred embodiment position 1 to 6 of said HCVR consists of SEQ ID NO:50.

In a further embodiment, said LC CDR1 comprises or preferably consists of the peptide of any one of SEQ ID NOs 5, 6 and 7; (b) said LC CDR2 comprises or preferably consists of the peptide of SEQ ID NO:8; and (c) said LC CDR3 comprises or preferably consists of the peptide of any one of SEQ ID NOs 9 and 10.

In a further embodiment said LCVR comprises a framework, wherein said framework is a product of a member of the V lambda family of V-gene segments, preferably of the V lambda 1 family of V-gene segments, combined with a J lambda gene segment.

In a preferred embodiment said LC CDR1 consists of the peptide of SEQ ID NO:5; (b) said LC CDR2 consists of the peptide of SEQ ID NO:8; and (c) said LC CDR3 consists of the peptide of SEQ ID NO:9.

In a further preferred embodiment (a) said LC CDR1 consists of the peptide of SEQ ID NO:6; (b) said LC CDR2 consists of the peptide of SEQ ID NO:8; and (c) said LC CDR3 consists of the peptide of SEQ ID NO:10. In a further preferred embodiment (a) said LC CDR1 consists of the peptide of SEQ ID NO:7; (b) said LC CDR2 consists of the peptide of SEQ ID NO:8; and (c) said LC CDR3 consists of the peptide of SEQ ID NO:10. In a further preferred embodiment (a) said LC CDR1 consists of the peptide of SEQ ID NO:5; (b) said LC CDR2 consists of the peptide of SEQ ID NO:8; and (c) said LC CDR3 consists of the peptide of SEQ ID NO:10.

In a very preferred embodiment position 5 to 107 of said LCVR consist of the peptide of any one of SEQ ID NOs 26, 31, 35, 37, and 41. In a further very preferred embodiment position 5 to 107 of said LCVR is encoded by the nucleic acid of any one of SEQ ID NOs 25, 30, 34, 36, and 40. In a further preferred embodiment position 1 to 4 of said LCVR consists of SEQ ID NO:51. In a further preferred embodiment position 108 to 110 of said LCVR consists of SEQ ID NO:53.

In a further very preferred embodiment (a) position 7 to 117 of said HCVR consist of the peptide of SEQ ID NO:24, and wherein position 5 to 107 of said LCVR consist of the peptide of SEQ ID NO:26; (b) position 7 to 117 of said HCVR consist of the peptide of SEQ ID NO:28, and wherein position 5 to 107 of said LCVR consist of the peptide of SEQ ID NO:31; (c) position 7 to 117 of said HCVR consist of the peptide of SEQ ID NO:33, and wherein position 5 to 107 of said LCVR consist of the peptide of SEQ ID NO:35; (d) position 7 to 117 of said HCVR consist of the peptide of SEQ ID NO:28, and wherein position 5 to 107 of said LCVR consist of the peptide of SEQ ID NO:37; or (e) position 7 to 117 of said HCVR consist of the peptide of SEQ ID NO:39, and wherein position 5 to 107 of said LCVR consist of the peptide of SEQ ID NO:41. In again a further very preferred embodiment (a) position 7 to 117 of said HCVR consist of the peptide of SEQ ID NO:24, and wherein position 5 to 107 of said LCVR consist of the peptide of SEQ ID NO:26.

In a further preferred embodiment, said human monoclonal antibody specifically binding nicotine comprises at least one HCVR and at least one LCVR, wherein position 7 to 117 of said HCVR is at least 80%, preferably 85%, more preferably 90%, again more preferably 95%, even more preferably at least 96%, still more preferably 97%, again still more preferably 98%, again still more preferably 99% and most preferably 100% identical to position 7 to 117 of SEQ ID NOs 24, 28, 33, and 39, preferably to position 7 to 117 of SEQ ID NO:24; and wherein position 5 to 107 of said LCVR is at least 80%, preferably 85%, more preferably 90%, again more preferably 95%, even more preferably at least 96%, still more preferably 97%, again still more preferably 98%, again still more preferably 99% and most preferably 100% identical to position 5 to 107 of SEQ ID NOs 26, 31, 35, 37, and 41, preferably to position 5 to 107 of SEQ ID NO:26.

Whether the amino acid sequence of a peptide or polypeptide has an amino acid sequence that is at least 80%, 85%, 90%, 95%, 97% or 99% identical to another, can be determined conventionally using known computer programs such the Bestfit program In another preferred embodiment, said human monoclonal antibody specifically binding nicotine comprises at least one HCVR and at least one LCVR, wherein position 7 to 117 of said HCVR is at least 80%, preferably 85%, more preferably 90%, again more preferably 95%, even more preferably at least 96%, still more preferably 97%, again still more preferably 98%, again still more preferably 99% and most preferably 100% identical to position 7 to 117 of SEQ ID NOs 24, 28, 33, and 39, preferably to position 7 to 117 of SEQ ID NO:24; and wherein position 5 to 107 of said LCVR is at least 80%, preferably 85%, more preferably 90%, again more preferably 95%, even more preferably at least 96%, still more preferably 97%, again still more preferably 98%, again still more preferably 99% and most preferably 100% identical to position 5 to 107 of SEQ ID NOs 26, 31, 35, 37, and 41, preferably to position 5 to 107 of SEQ ID NO:26, and wherein said HCVR comprises (i) one HC CDR1 consisting of the peptide of SEQ ID NO:1; (ii) one HC CDR2 consisting of the peptide of SEQ ID NO:2; and (iii) one HC CDR3 consisting of the peptide of SEQ ID NO:3, and wherein said LCVR comprises (i) one LC CDR1 consisting of the peptide of SEQ ID NO:5; (ii) one LC CDR2 consisting of the peptide of SEQ ID NO:8; (iii) one LC CDR3 consisting of the peptide of SEQ ID NO:9.

In a further very preferred embodiment (a) position 7 to 117 of said HCVR is encoded by the nucleic acid of SEQ ID NO:23, and wherein position 5 to 107 of said LCVR is encoded by the nucleic acid of SEQ ID NO:25; (b) position 7 to 117 of said HCVR is encoded by the nucleic acid of SEQ ID NO:27, and wherein position 5 to 107 of said LCVR is encoded by the nucleic acid of SEQ ID NO:30; (c) position 7 to 117 of said HCVR is encoded by the nucleic acid of SEQ ID NO:32, and wherein position 5 to 107 of said LCVR is encoded by the nucleic acid of SEQ ID NO:34; (d) position 7 to 117 of said HCVR is encoded by the nucleic acid of SEQ ID NO:29, and wherein position 5 to 107 of said LCVR is encoded by the nucleic acid of SEQ ID NO:36; or (e) position 7 to 117 of said HCVR is encoded by the nucleic acid of SEQ ID NO:38, and wherein position 5 to 107 of said LCVR is encoded by the nucleic acid of SEQ ID NO:40.

The antibodies of the invention may be produced in the format of single chain antibodies. Thus, in a further very embodiment said monoclonal antibody comprises or preferably consists of the peptide of any one of SEQ ID NOs 60, 62, 64, 66, and 68. In a further preferred embodiment said monoclonal antibody is a single chain antibody, wherein preferably said single chain antibody comprises or preferably consists of the peptide of any one of SEQ ID NOs 60, 62, 64, 66, and 68. In a further very preferred embodiment said monoclonal antibody comprises or preferably consists of a peptide, wherein said peptide is encoded by the nucleic acid of any one of SEQ ID NOs 59, 61, 63, 65, and 67.

In a further preferred embodiment said monoclonal antibody is expressed as a IgG, preferably as a IgG2. Thus, in a further preferred embodiment said monoclonal antibody comprises at least one gamma 2 heavy chain, wherein preferably said gamma 2 heavy chain comprises or preferably consists of the peptide of any one of SEQ ID NOs 73, 75, 77, and 80. In a further preferred embodiment said monoclonal antibody comprises at least one lambda light chain, wherein preferably said lambda light chain comprises or preferably consists of the peptide of any one of SEQ ID NOs 74, 76, 78, 79, and 81.

In a very preferred embodiment said monoclonal antibody comprises at least one gamma 2 heavy chain and at least one lambda light chain, wherein (a) said gamma 2 heavy chain comprises or preferably consists of the peptide of SEQ ID NO:73, and wherein said lambda light chain comprises or preferably consists of the peptide of SEQ ID NO:74; (b) said gamma 2 heavy chain comprises or preferably consists of the peptide of SEQ ID NO:75, and wherein said lambda light chain comprises or preferably consists of the peptide of SEQ ID NO:76; (c) said gamma 2 heavy chain comprises or preferably consists of the peptide of SEQ ID NO:77, and wherein said lambda light chain comprises or preferably consists of the peptide of SEQ ID NO:78; (d) said gamma 2 heavy chain comprises or preferably consists of the peptide of SEQ ID NO:75, and wherein said lambda light chain comprises or preferably consists of the peptide of SEQ ID NO:79; or (e) said gamma 2 heavy chain comprises or preferably consists of the peptide of SEQ ID NO:80, and wherein said lambda light chain comprises or preferably consists of the peptide of SEQ ID NO:81.

In a further preferred embodiment said monoclonal antibody comprises a light chain constant region (LCCR), wherein preferably said LCCR is a lambda LCCR.

In another embodiment (a) said HC CDR1 comprises or preferably consists of the peptide of SEQ ID NO:11; (b) said HC CDR2 comprises or preferably consists of the peptide of SEQ ID NO:12; and (c) said HC CDR3 comprises or preferably consists of the peptide of SEQ ID NO:13, wherein preferably said HCVR comprises a framework, wherein said framework is a product of a member of the VH family of V-gene segments, preferably of the VH4 family of V-gene segments, combined with a JH-gene segment.

In a preferred embodiment (a) said HC CDR1 consists of the peptide of SEQ ID NO:11; (b) said HC CDR2 consists of the peptide of SEQ ID NO:12; and (c) said HC CDR3 consists of the peptide of SEQ ID NO:13.

In a further preferred embodiment position 7 to 121 of said HCVR consist of the peptide of SEQ ID NO:43. In a further preferred embodiment position 7 to 121 of said HCVR is encoded by the nucleic acid of SEQ ID NO:42. And in a further preferred embodiment position 1 to 6 of said HCVR consists of SEQ ID NO:50.

In a further preferred embodiment (a) said LC CDR1 comprises or preferably consists of the peptide of SEQ ID NO:14; (b) said LC CDR2 comprises or preferably consists of the peptide of SEQ ID NO:15; and (c) wherein said LC CDR3 comprises or preferably consists of the peptide of SEQ ID NO:16, wherein preferably said LCVR comprises a framework, wherein further preferably said framework is a product of a member of the V kappa family of V-gene segments, preferably of the V kappa 3 family of V-gene segments, combined with a J kappa gene segment.

In a further preferred embodiment (a) said LC CDR1 consists of the peptide of SEQ ID NO:14; (b) said LC CDR2 consists of the peptide of SEQ ID NO:15; and (c) said LC CDR3 consists of the peptide of SEQ ID NO:16. In a further preferred embodiment position 5 to 104 of said LCVR consist of the peptide of SEQ ID NO:45. In a further preferred embodiment position 5 to 104 of said LCVR is encoded by the nucleic acid of SEQ ID NO:44. And in a further preferred embodiment 1 to 4 of said LCVR consists of SEQ ID NO:52. And in a further preferred embodiment position 105 to 107 of said LCVR consists of SEQ ID NO:54.

In a very preferred embodiment position 7 to 121 of said HCVR consist of the peptide of SEQ ID NO:43, and position 5 to 104 of said LCVR consist of the peptide of SEQ ID NO:45. In a very preferred embodiment position 7 to 121 of said HCVR is encoded by the nucleic acid of SEQ ID NO:42, and position 5 to 104 of said LCVR is encoded by the nucleic acid of SEQ ID NO:44.

In a further very preferred embodiment said monoclonal antibody comprises or preferably consists of the peptide of SEQ ID NO:70. In a further very preferred embodiment said monoclonal antibody is a single chain antibody, wherein said single chain antibody comprises or preferably consists of the peptide of SEQ ID NO:70. In a further very preferred embodiment said monoclonal antibody comprises or preferably consists of a peptide, wherein said peptide is encoded by the nucleic acid of SEQ ID NO:69.

In a further very preferred embodiment said monoclonal antibody comprises at least one gamma 2 heavy chain, wherein said gamma 2 heavy chain comprises or preferably consists of the peptide of SEQ ID NO:82. In a further very preferred embodiment said monoclonal antibody comprises at least one kappa light chain, wherein said kappa light chain comprises or preferably consists of the peptide of SEQ ID NO:83. In a further very preferred embodiment said monoclonal antibody comprises at least one gamma 2 heavy chain and at least one kappa light chain, wherein said gamma 2 heavy chain comprises or preferably consists of the peptide of SEQ ID NO:82, and wherein said kappa light chain comprises or preferably consists of the peptide of SEQ ID NO:83.

In a further preferred embodiment said monoclonal antibody comprises a light chain constant region (LCCR), wherein preferably said LCCR is a kappa LCCR.

In a further embodiment (a) said HC CDR1 comprises or preferably consists of the peptide of SEQ ID NO:17; (b) said HC CDR2 comprises or preferably consists of the peptide of SEQ ID NO:18; and (c) said HC CDR3 comprises or preferably consists of the peptide of SEQ ID NO:19, wherein preferably said HCVR comprises a framework, wherein said framework is a product of a member of the VH family of V-gene segments, preferably of the VH4 family of V-gene segments, combined with a JH-gene segment.

In a preferred embodiment (a) said HC CDR1 consists of the peptide of SEQ ID NO:17; (b) said HC CDR2 consists of the peptide of SEQ ID NO:18; and (c) said HC CDR3 consists of the peptide of SEQ ID NO:19. In a very preferred embodiment position 7 to 121 of said HCVR consist of the peptide of SEQ ID NO:47. In a further very preferred embodiment position 7 to 121 of said HCVR is encoded by the nucleic acid of SEQ ID NO:46. In a further preferred embodiment position 1 to 6 of said HCVR consists of SEQ ID NO:50.

In a further embodiment (a) said LC CDR1 comprises or preferably consists of the peptide of SEQ ID NO:20; (b) said LC CDR2 comprises or preferably consists of the peptide of SEQ ID NO:21; and (c) wherein said LC CDR3 comprises or preferably consists of the peptide of SEQ ID NO:22, wherein preferably said LCVR comprises a framework, wherein said framework is a product of a member of the V lambda family of V-gene segments, preferably of the V lambda 1 family of V-gene segments, combined with a J lambda gene segment.

In a preferred embodiment (a) said LC CDR1 consists of the peptide of SEQ ID NO:20; (b) said LC CDR2 consists of the peptide of SEQ ID NO:21; and (c) said LC CDR3 consists of the peptide of SEQ ID NO:22.

In a further preferred embodiment position 5 to 107 of said LCVR consist of the peptide of SEQ ID NO:49. In a further preferred embodiment position 5 to 107 of said LCVR is encoded by the nucleic acid of SEQ ID NO:48. And in a preferred embodiment position 1 to 4 of said LCVR consists of SEQ ID NO:51. And in a preferred embodiment position 108 to 110 of said LCVR consists of SEQ ID NO:53.

In a very preferred embodiment position 7 to 121 of said HCVR consist of the peptide of SEQ ID NO:47, and position 5 to 107 of said LCVR consist of the peptide of SEQ ID NO:49.

In a very preferred embodiment position 7 to 121 of said HCVR is encoded by the nucleic acid of SEQ ID NO:46, and position 5 to 107 of said LCVR is encoded by the nucleic acid of SEQ ID NO:48.

In a preferred embodiment said monoclonal antibody comprises or preferably consists of the peptide of SEQ ID NO:72. In further preferred embodiment said monoclonal antibody is a single chain antibody, wherein said single chain antibody comprises or preferably consists of the peptide of SEQ ID NO:72. In a preferred embodiment said monoclonal antibody comprises or preferably consists of a peptide, wherein said peptide is encoded by the nucleic acid of SEQ ID NO:71.

In a further preferred embodiment said monoclonal antibody comprises at least one gamma 2 heavy chain, wherein preferably said gamma 2 heavy chain comprises or preferably consists of the peptide of SEQ ID NO:84.

In a further preferred embodiment said monoclonal antibody comprises at least one lambda light chain, wherein said lambda light chain comprises or preferably consists of the peptide of SEQ ID NO:85.

In a very preferred embodiment said monoclonal antibody comprises at least one gamma 2 heavy chain and at least one lambda light chain, wherein said gamma 2 heavy chain comprises or preferably consists of the peptide of SEQ ID NO:84, and wherein said lambda light chain comprises or preferably consists of the peptide of SEQ ID NO:85.

In a further preferred embodiment said monoclonal antibody comprises a light chain constant region (LCCR), wherein preferably said LCCR is a lambda LCCR.

A monoclonal antibody of the invention can be recombinantly produced in any naturally occurring or synthetic format. The following embodiments thus explicitly refer to all aspects and embodiments of the invention. In one embodiment said monoclonal antibody is a recombinant antibody. In a preferred embodiment the monoclonal antibody of the invention is an antibody selected from the group consisting of: (a) single chain antibody, preferably scFv; (b) Fab fragment; (c) F(ab')2 fragment; (d) scFv-Fc fusion; (e) IgG1; (f) IgG2; (g) IgG3; (h) IgG4; (i) IgA; (j) IgE; (k) IgM; (l) IgD; and (m) diabody.

In a preferred embodiment said monoclonal antibody comprises or preferably consists of exactly one HCVR and/or of exactly one LCVR.

In a further preferred embodiment said monoclonal antibody comprises a heavy chain constant region (HCCR), wherein preferably said HCCR is selected from (a) gamma HCCR, (b) alpha HCCR, (c) epsilon HCCR, (d) my HCCR, and (e) delta HCCR, wherein further preferably said HCCR, and preferably said gamma HCCR, alpha HCCR, epsilon HCCR, my HCCR, and/or delta HCCR, is a human HCCR.

In still further preferred embodiment said HCCR is a gamma HCCR, wherein preferably said gamma HCCR is selected from (a) gamma 1 HCCR; (b) gamma 2 HCCR; (d) gamma 3 HCCR; and (c) gamma 4 HCCR; wherein preferably said gamma HCCR is a gamma 2 HCCR.

In a further preferred embodiment said monoclonal antibody comprises a light chain constant region (LCCR), wherein preferably said LCCR is selected from (a) lambda LCCR; and (b) kappa LCCR, wherein further preferably said LCCR, and most preferably said lambda LCCR and/or said kappa LCCR, is a human LCCR.

Preferably, the monoclonal antibody of the invention is an IgG2, most preferably a fully human IgG2. Thus, in a preferred embodiment said monoclonal antibody comprises two, preferably exactly two, of said gamma 2 heavy chains, wherein further preferably said two, preferably said exactly two of said gamma 2 heavy chains are identical.

In a further preferred embodiment said monoclonal antibody comprises two, preferably exactly two light chains, wherein preferably said light chains are selected from (a) lambda light chain; and (b) kappa light chain; wherein still further preferably said two, preferably said exactly two of said light chains are identical.

Preferably, said monoclonal antibody comprises at least one HCVR, wherein said HCVR comprises: (a) one HC CDR1, wherein said HC CDR1 comprises or preferably consists of the peptide of any one of SEQ ID NOs 1, 11 and 17, very preferably consists of the peptide of SEQ ID NO:1, and wherein preferably said HC CDR1 is located at CDR1 position within the framework of said HCVR; (b) one HC CDR2, wherein said HC CDR2 comprises or preferably consists of the peptide of any one of SEQ ID NOs 2, 12, and 18, very preferably consists of the peptide of SEQ ID NO:2, and wherein preferably said HC CDR2 is located at CDR2 position within the framework of said HCVR; and/or (c) one HC CDR3, wherein said HC CDR3 comprises or preferably consists of the peptide of any one of SEQ ID NOs 3, 4, 13 and 19, very preferably consists of the peptide of SEQ ID NO:3, and wherein preferably said HC CDR3 is located at CDR3 position within the framework of said HCVR; and/or, preferably and, wherein said monoclonal antibody comprises at least one LCVR, wherein said LCVR comprises: (a) one LC CDR1, wherein said LC CDR1 comprises or preferably consists of the peptide of any one of SEQ ID NOs 5, 6, 7, 14 and 20; very preferably consists of the peptide of SEQ ID NO:5, and wherein preferably said LC CDR1 is located at CDR1 position within the framework of said LCVR; (b) one LC CDR2, wherein said LC CDR2 comprises or preferably consists of the peptide of any one of SEQ ID NOs 8, 15 and 21, very preferably consists of the peptide of SEQ ID NO:8, and wherein preferably said LC CDR2 is located at CDR2 position within the framework of said LCVR; and/or (c) one LC CDR3, wherein said LC CDR3 comprises or preferably consists of the peptide of any one of SEQ ID NOs 9, 10, 16 and 22, very preferably consists of the peptide of SEQ ID NO:9, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:3, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:9, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 0.1 to 10 nM, preferably 1 to 10 nM; and wherein the dissociation constant Kd of said binding of said monoclonal antibody to said (R)-(+)-nicotine is 0.1 to 10 nM, preferably 1 to 10 nM, wherein preferably Kd is determined using said monoclonal antibody in the IgG2 format; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:3, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:9, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 0.1 to 10 nM, preferably 1 to 10 nM; and wherein the dissociation constant Kd of said binding of said monoclonal antibody to said (R)-(+)-nicotine is 0.1 to 10 nM, preferably 1 to 10 nM, wherein preferably Kd is determined using said monoclonal antibody in the IgG2 format; and wherein said monoclonal antibody comprises a gamma 2 heavy chain and a lambda light chain, wherein said gamma 2 heavy chain comprises or preferably consists of the peptide of SEQ ID NO:73, and wherein said lambda light chain comprises or preferably consists of the peptide of SEQ ID NO:74.

In another preferred embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is equal to, preferably 2 to 5 times higher, more preferably about 2 times higher, and most preferably 2 times higher than said binding of said monoclonal antibody to said (R)-(+)-nicotine, wherein preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:3, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:9, and wherein preferably said LC CDR3 is located at CDR3 position within the framework of said LCVR.

Preferably, said monoclonal antibody comprises at least one HCVR, wherein said HCVR comprises: (a) one HC CDR1, wherein said HC CDR1 comprises or preferably consists of the peptide of any one of SEQ ID NOs 1, 11 and 17, very preferably consists of the peptide of SEQ ID NO:1, and wherein preferably said HC CDR1 is located at CDR1 position within the framework of said HCVR; (b) one HC CDR2, wherein said HC CDR2 comprises or preferably consists of the peptide of any one of SEQ ID NOs 2, 12, and 18, very preferably consists of the peptide of SEQ ID NO:2, and wherein preferably said HC CDR2 is located at CDR2 position within the framework of said HCVR; and/or (c) one HC CDR3, wherein said HC CDR3 comprises or preferably consists of the peptide of any one of SEQ ID NOs 3, 4, 13 and 19, very preferably consists of the peptide of SEQ ID NO:3, and wherein preferably said HC CDR3 is located at CDR3 position within the framework of said HCVR; and/or, preferably and, wherein said monoclonal antibody comprises at least one LCVR, wherein said LCVR comprises: (a) one LC CDR1, wherein said LC CDR1 comprises or preferably consists of the peptide of any one of SEQ ID NOs 5, 6, 7, 14 and 20; very preferably consists of the peptide of SEQ ID NO:5, and wherein preferably said LC CDR1 is located at CDR1 position within the framework of said LCVR; (b) one LC CDR2, wherein said LC CDR2 comprises or preferably consists of the peptide of any one of SEQ ID NOs 8, 15 and 21, very preferably consists of the peptide of SEQ ID NO:8, and wherein preferably said LC CDR2 is located at CDR2 position within the framework of said LCVR; and/or (c) one LC CDR3, wherein said LC CDR3 comprises or preferably consists of the peptide of any one of SEQ ID NOs 9, 10, 16 and 22, very preferably consists of the peptide of SEQ ID NO:9, and wherein preferably said LC CDR3 is located at CDR3 position within the framework of said LCVR.

In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 10 nM, wherein further preferably Kd is determined using said monoclonal antibody in the IgG2 format; and wherein the dissociation constant Kd of said binding of said monoclonal antibody to said (R)-(+)-nicotine is lower than 10 nM, wherein further preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:3, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:9, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 10 to 100 nM, preferably 25 to 75 nM, most preferably 25 to 35 nM; and wherein the dissociation constant Kd of said binding of said monoclonal antibody to said (R)-(+)-nicotine is 0.1 to 10 nM, preferably 1 to 10 nM, wherein preferably Kd is determined using said monoclonal antibody in the IgG2 format; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 10 to 100 nM, preferably 25 to 75 nM, most preferably 25 to 35 nM; and wherein the dissociation constant Kd of said binding of said monoclonal antibody to said (R)-(+)-nicotine is 0.1 to 10 nM, preferably 1 to 10 nM, wherein preferably Kd is determined using said monoclonal antibody in the IgG2 format; said monoclonal antibody comprises a gamma 2 heavy chain and a lambda light chain, wherein said gamma 2 heavy chain comprises or preferably consists of the peptide of SEQ ID NO:75, and wherein said lambda light chain comprises or preferably consists of the peptide of SEQ ID NO:76.

In another preferred embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is equal to, preferably 2 to 7 times higher, more preferably about 5 times higher, and most preferably 5 times higher than said binding of said monoclonal antibody to said (R)-(+)-nicotine, wherein preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 40 nM, wherein further preferably Kd is determined using said monoclonal antibody in the IgG2 format; and wherein the dissociation constant Kd of said binding of said monoclonal antibody to said (R)-(+)-nicotine is lower than 10 nM, wherein further preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:7, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 10 to 100 nM, preferably 25 to 75 nM; and wherein the dissociation constant Kd of said binding of said monoclonal antibody to said (R)-(+)-nicotine is 1 to 20 nM, preferably 10 to 15 nM, wherein preferably Kd is determined using said monoclonal antibody in the IgG2 format; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:7, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 10 to 100 nM, preferably 25 to 75 nM; and wherein the dissociation constant Kd of said binding of said monoclonal antibody to said (R)-(+)-nicotine is 1 to 20 nM, preferably 10 to 15 nM, wherein preferably Kd is determined using said monoclonal antibody in the IgG2 format; and wherein said monoclonal antibody comprises a gamma 2 heavy chain and a lambda light chain, wherein said gamma 2 heavy chain comprises or preferably consists of the peptide of SEQ ID NO:77, and wherein said lambda light chain comprises or preferably consists of the peptide of SEQ ID NO:78.

In another preferred embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is equal to, preferably 2 to 7 times higher, more preferably about 5 times higher, and most preferably 5 times higher than said binding of said monoclonal antibody to said (R)-(+)-nicotine, wherein preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:7, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 75 nM, wherein further preferably Kd is determined using said monoclonal antibody in the IgG2 format; and wherein the dissociation constant Kd of said binding of said monoclonal antibody to said (R)-(+)-nicotine is lower than 15 nM, wherein further preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:7, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 20 to 60 nM, preferably 30 to 50 nM; and wherein the dissociation constant Kd of said binding of said monoclonal antibody to said (R)-(+)-nicotine is 0.1 to 10 nM, preferably 1 to 10 nM, wherein preferably Kd is determined using said monoclonal antibody in the IgG2 format; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 20 to 60 nM, preferably 30 to 50 nM; and wherein the dissociation constant Kd of said binding of said monoclonal antibody to said (R)-(+)-nicotine is 0.1 to 10 nM, preferably 1 to 10 nM, wherein preferably Kd is determined using said monoclonal antibody in the IgG2 format; wherein said monoclonal antibody comprises a gamma 2 heavy chain and a lambda light chain, wherein said gamma 2 heavy chain comprises or preferably consists of the peptide of SEQ ID NO:75, and wherein said lambda light chain comprises or preferably consists of the peptide of SEQ ID NO:79.

In another preferred embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is equal to, preferably 2 to 7 times higher, more preferably about 4 times higher, and most preferably 4 times higher than said binding of said monoclonal antibody to said (R)-(+)-nicotine, wherein preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 60 nM, wherein further preferably Kd is determined using said monoclonal antibody in the IgG2 format; and wherein the dissociation constant Kd of said binding of said monoclonal antibody to said (R)-(+)-nicotine is lower than 10 nM, wherein further preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:5, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 20 to 80 nM, preferably 30 to 75 nM; and wherein the dissociation constant Kd of said binding of said monoclonal antibody to said (R)-(+)-nicotine is 0.1 to 15 nM, preferably 1 to 12 nM, wherein preferably Kd is determined using said monoclonal antibody in the IgG2 format; and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

In a very preferred further embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 20 to 80 nM, preferably 30 to 75 nM; and wherein the dissociation constant Kd of said binding of said monoclonal antibody to said (R)-(+)-nicotine is 0.1 to 15 nM, preferably 1 to 12 nM, wherein preferably Kd is determined using said monoclonal antibody in the IgG2 format; wherein said monoclonal antibody comprises a gamma 2 heavy chain and a lambda light chain, wherein said gamma 2 heavy chain comprises or preferably consists of the peptide of SEQ ID NO:80, and wherein said lambda light chain comprises or preferably consists of the peptide of SEQ ID NO:81.

In another preferred embodiment, the invention relates to a monoclonal antibody, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is equal to, preferably 2 to 7 times higher, more preferably about 3 times higher, and most preferably 3 times higher than said binding of said monoclonal antibody to said (R)-(+)-nicotine, wherein preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR. In again a still very preferred embodiment said monoclonal antibody is binding (S)-(−)-nicotine and (R)-(+)-nicotine, wherein the dissociation constant Kd of said binding of said monoclonal antibody to said (S)-(−)-nicotine is lower than 80 nM, wherein further preferably Kd is determined using said monoclonal antibody in the IgG2 format; and wherein the dissociation constant Kd of said binding of said monoclonal antibody to said (R)-(+)-nicotine is lower than 15 nM, wherein further preferably Kd is determined using said monoclonal antibody in the IgG2 format, and wherein said monoclonal antibody comprises at least one HCVR, wherein said HCVR comprises: (a) one HC CDR1, wherein said HC CDR1 consists of the peptide of SEQ ID NO:1, and wherein preferably said HC CDR1 is located at CDR1 position within the framework of said HCVR; (b) one HC CDR2, wherein said HC CDR2 consists of the peptide of SEQ ID NO:2, and wherein preferably said HC CDR2 is located at CDR2 position within the framework of said HCVR; and (c) one HC CDR3, wherein said HC CDR3 consists of the peptide of SEQ ID NO:4, and wherein preferably said HC CDR3 is located at CDR3 position within the framework of said HCVR; and, wherein said monoclonal antibody comprises at least one LCVR, wherein said LCVR comprises: (a) one LC CDR1, wherein said LC CDR1 consists of the peptide of SEQ ID NO:6, and wherein preferably said LC CDR1 is located at CDR1 position within the framework of said LCVR; (b) one LC CDR2, wherein said LC CDR2 consists of the peptide of SEQ ID NO:8, and wherein preferably said LC CDR2 is located at CDR2 position within the framework of said LCVR; and (c) one LC CDR3, wherein said LC CDR3 consists of the peptide of SEQ ID NO:10, and wherein preferably said LC CDR3 is located at CDR3 position within the framework of said LCVR.

It is to be understood that it is well within the skill of the artisan to use a HCVR of a first antibody specifically binding nicotine, to select a corresponding LCVR from a suitable source, and to create a second antibody, wherein said second antibody comprises said HCVR of said first antibody and the selected LCVR, and wherein said second antibody is capable of binding nicotine with about the same specificity as said first antibody ("chain shuffling", see Example 9). It is furthermore apparent for the artisan that in an analogous manner the LCVR of a first antibody can be used to select a corresponding HCVR from a suitable source. Suitable sources for the amplification of LCVRs and/or HCVRs are, for example, cDNA from naive human B cells, cDNA from B cells of a human subject immunized with a Nicotine-carrier conjugate, and fully synthetic libraries, such as Morphosys' HuCAL library. These methods are described in detail in Kang A S et al. (Proc Natl Acad Sci USA 88, 11120-11123, 1991), Marks J D et al. (Biotechnology (NY) 10, 779-783, 1992), and Jespers et al. (Biotechnology (NY) 12, 899-903, 1994).

Thus, one further aspect of the invention is a HCVR of a monoclonal antibody, wherein said monoclonal antibody is a human monoclonal antibody, and wherein said monoclonal antibody is specifically binding (S)-(−)-nicotine and (R)-(+)-nicotine, and wherein said HCVR comprises: (a) one HC CDR1, wherein said HC CDR1 consists of the peptide of SEQ ID NO:1; (b) one HC CDR2, wherein said HC CDR2 consists of the peptide of SEQ ID NO:2; and (c) one HC CDR3, wherein said HC CDR3 consists of the peptide of any one of SEQ ID NOs 3 and 4.

In a preferred embodiment position 7 to 117 of said HCVR consists of the peptide of any one of SEQ ID NOs 24, 28, 33, and 39.

A further aspect of the invention is a LCVR of a monoclonal antibody, wherein said monoclonal antibody is a human monoclonal antibody, and wherein said monoclonal antibody is specifically binding (S)-(−)-nicotine and (R)-(+)-nicotine, and wherein said LCVR comprises: (a) one LC CDR1, wherein said LC CDR1 consists of the peptide of any one of SEQ ID NOs 5, 6, and 7; (b) one LC CDR2, wherein said LC CDR2 consists of the peptide of SEQ ID NO:8; (c) one LC CDR3, wherein said LC CDR3 consists of the peptide of any one of SEQ ID NOs 9 and 10.

In a preferred embodiment position 5 to 107 of said LCVR consist of the peptide of any one of SEQ ID NOs 26, 31, 35, 37, and 41.

In a further aspect, the invention relates a nucleic acid molecule encoding a variable region or the invention, a monoclonal antibody of the invention or an individual chain thereof. In a preferred embodiment said nucleic acid molecule is encoding a peptide selected from (a) a HCVR of the invention, wherein preferably said HCVR comprises or preferably consists of the peptide of any one of SEQ ID NOs 24, 28, 33, 39, 43, and 47; (b) a LCVR of the invention, wherein preferably said LCVR comprises or preferably consists of the peptide of any one of SEQ ID NOs 26, 31, 35, 37, 41, 45, and 49; (c) a single chain antibody of the invention, wherein preferably said single chain antibody comprises or preferably consists of the peptide of any one of SEQ ID NOs 60, 62, 64, 66, 68, 70, and 72; (d) a gamma 2 heavy chain of the invention, wherein preferably said gamma 2 heavy chain comprises or preferably consists of the peptide of any one of SEQ ID NOs 73, 75, 77, 80, 82, and 84; (e) a lambda light chain of the invention, wherein preferably said lambda light chain comprises or preferably consists of the peptide of any one of SEQ ID NOs 74, 76, 78, 79, 81, and 85; (f) a kappa light chain of the invention, wherein preferably said kappa light chain comprises or preferably consists of the peptide of SEQ ID NO:83; and (g) a monoclonal antibody of the invention.

In a further preferred embodiment said nucleic acid molecule comprises or consists of the nucleotide sequence of any one of SEQ ID NOs 23, 27, 29, 32, 38, 42 and 46; and/or of the nucleotide sequence of any one of SEQ ID NOs 25, 30, 34, 36, 40, 44, and 48; and/or of the nucleotide sequence of any one of SEQ ID NOs 59, 61, 63, 65, 67, 69, and 71.

In a further aspect, the invention relates to an expression vector comprising at least one nucleic acid molecule of the invention. Expression vectors suitable for the expression of the monoclonal antibodies of the invention are disclosed, for example, in PCT/EP2007/061570.

In a further aspect, the invention relates to a host cell comprising at least one nucleic acid molecule or at least one expression vector of the invention, wherein preferably said host cell is a bacteria cell or an eukaryotic cell. In a preferred embodiment said host cell is a eukaryotic cell selected from (a) yeast cell, (b) insect cell; and (c) mammalian cell, wherein preferably said mammalian cell is selected from HEK-293T cell, CHO cell, and COS cell. Very preferably, said mammalian cells is a HEK-293T cell.

The monoclonal antibody of the invention can be incorporated into compositions suitable for administration to a subject. Thus, in a further aspect, the invention relates to a pharmaceutical composition comprising at least one monoclonal antibody of the invention, wherein preferably said pharmaceutical composition further comprises a pharmaceutically acceptable carrier, diluent or excipient. Pharmaceutically acceptable carriers, diluents and excipients are disclosed, for example, in Remington, The Science and Practice of Pharmacy, 19$^{th}$ edition, Gennaro (ed.), Mack publishing Co., Easton, Pa., 1995. Pharmaceutical compositions of the invention are administered in a single dose or in multiple doses.

In a preferred embodiment said pharmaceutical composition, further comprises at least one further antibody, wherein preferably said at least one further antibody is specifically binding nicotine.

The monoclonal antibodies of the invention may be used in passive immunization, preferably of humans, and further preferably against nicotine. The monoclonal antibodies of the invention are therefore useful in the treatment of nicotine addiction. In a further aspect, the invention relates to a method of passive immunization, preferably against nicotine, said method comprising administering to a subject an effective amount of the monoclonal antibody of the invention or an effective amount of the pharmaceutical composition of the invention.

The monoclonal antibody and/or the pharmaceutical composition of the invention are preferably administered to a subject, preferably to a human, using standard administration techniques, preferably selected from oral administration, intravenous administration, intraperitoneal administration, subcutaneous administration, pulmonary administration, transdermal administration, intramuscular administration, intranasal administration, buccal administration, sublingual administration, and suppository administration.

In a further aspect, the invention relates to a method of treating nicotine addiction, said method comprising administering to a subject an effective amount of the monoclonal antibody of the invention or an effective amount of the pharmaceutical composition of the invention, wherein preferably said subject is a human, and wherein further preferably said subject is addicted to nicotine.

In a further aspect, the invention relates to the monoclonal antibody of the invention or to the pharmaceutical composition of the invention, for use in passive immunization, preferably against nicotine, preferably in a human, wherein further preferably said monoclonal antibody is to be administered to said human.

In a further aspect, the invention relates to the monoclonal antibody of the invention or to the pharmaceutical composition of the invention, for use in the treatment of nicotine addiction, preferably in a human.

In a further aspect, the invention relates to the use of the monoclonal antibody of the invention in the manufacture of a medicament for passive immunization, preferably against nicotine.

In a further aspect, the invention relates to a monoclonal antibody of the invention for use in passive immunization, preferably against nicotine.

In a further aspect, the invention relates to the use of the monoclonal antibody of the invention in the manufacture of a medicament for the treatment of nicotine addiction, preferably in a human.

In a further aspect, the invention relates to a monoclonal antibody of the invention for use in a method of treating nicotine addiction, preferably in a human.

A further aspect of the invention is the use of an antibody of the invention in a method of quantitative and/or qualitative detection of nicotine, preferably in a blood sample and most preferably by ELISA.

It is to be understood that the all aspects of the invention relate to any monoclonal antibody which is disclosed herein.

EXAMPLES

Example 1

Identification of Nicotine-Specific Single-Chain Antibodies by Mammalian Cell Display Peripheral blood mononuclear cells (PBMC) were isolated from 32 ml of heparinized blood of a Qβ-Nicotine-vaccinated volunteer using the BD Vacutainer™ CPT™ Tube method (BD Bioscience). PBMC were pre-incubated with Alexa 647 nm-labeled Qβ (3 μg/ml) and mouse gamma globulin (10 ug/ml; Jackson ImmunoResearch) and then stained with: (1) Qβ-Nicotine (1 μg/ml) in combination with a Alexa 488 nm-labeled Qβ-specific mouse mAb (1 μg/ml) and a Alexa 488 nm-labeled Nicotine-specific mouse mAb (1 μg/ml); (2) PE-labeled mouse anti-human IgM (diluted 1:50; BD Biosciences Pharmingen), mouse anti-human IgD (diluted 1:100; BD Biosciences Pharmingen), mouse anti-human CD14 (diluted 1:50; BD Biosciences Pharmingen), and mouse anti-human CD3 (diluted 1:50; BD Biosciences Pharmingen) antibodies; and (4) PE-TexasRed-labeled mouse anti-human CD19 antibody (diluted 1:50; Caltag Laboratories). After staining, cells were washed and filtered, and 443 Nicotine-specific B cells (FL1-positive, FL2-negative, FL3-positive, FL4-negative) were sorted on a FACSVantage SE flow cytometer (Becton Dickinson).

Antigen-specific B cells were used for the construction of a Sindbis-based scFv cell surface display library essentially as described (see WO1999/025876A1 for Sindbis-based screening in general and PCT/EP2007/061570 for its application in antibody screening). Cells displaying Nicotine-specific scFv antibodies were isolated using RNase-Nicotine in combination with an RNase-specific rabbit polyclonal antibody (2.5 μg/ml; Abcam) and a FITC-labeled donkey anti-rabbit IgG antibody (1.5 μg/ml; Jackson ImmunoResearch). Each cell was sorted into a well of a 24-well plate containing 50% confluent BHK feeder cells. Upon virus spread (2 days post sorting), the infected cells were tested by FACS analysis for Nicotine-binding to identify virus clones encoding Nicotine-specific scFv antibodies.

Example 2

Gene Rescue, ELISA Screening and Sequencing of Nicotine-Specific Antibodies

The supernatants of BHK cells encoding putative Nicotine-specific antibodies, each containing a monoclonal recombinant Sindbis virus, were subjected to RT-PCR as described (see application PCT/EP2007/061570). The resulting PCR products, each comprising a scFv coding region, were digested with the restriction endonuclease SfiI and cloned into the expression vector pCEP-SP-Sfi-Fc (disclosed as SEQ ID NO:37 in application PCT/EP2007/061570), allowing for expression of scFv proteins fused to a C-terminal human Fc-γ1 domain under the control of a CMV promoter.

For ELISA analysis, each of the clones was transfected into HEK-293T cells in a 24-well plate format, using Lipofectamin 2000 (Invitrogen) according to the manufacturer's recommendations. 2-3 days post transfection, supernatants containing transiently expressed scFv-Fc fusion proteins were harvested. To check for Nicotine-specific binding, ELISA plates were coated with Nicotine-conjugated RNAse at a concentration of 4 µg/ml in phosphate-buffered saline (PBS) over night at 4° C. In parallel, scFv-Fc expression levels were monitored in by sandwich ELISA. For this, an identical set of plates was coated with Fcγ-specific, goat anti-human F(ab')2 antibody (Jackson ImmunoResearch Laboratories 109-006-098) at a concentration of 2.5 µg/ml. The plates were then washed with wash buffer (PBS/0.05% Tween) and blocked for 2 h at room temperature with 3% BSA in wash buffer. The plates were then washed again and incubated with 3-fold serial dilutions of the cell culture supernatants, starting at a dilution of 1/10. All dilutions were done in wash buffer. Plates were incubated at room temperature for 2 h and then extensively washed with wash buffer. Bound scFv-Fc fusion proteins were then detected by a 1 h incubation with a HRPO-labeled, Fcγ-specific, goat anti-human IgG antibody (Jackson ImmunoResearch Laboratories 109-035-098). After extensive washing with wash buffer, plates were developed with OPD solution (1 OPD tablet, 25 ml OPD buffer and 8 µl 30% $H_2O_2$) for 5 to 10 minutes and the reaction was stopped with 5% $H_2SO_4$ solution. Plates were then read at OD 450 nm on an ELISA reader (Biorad Benchmark).

ELISA-positive clones encoding Nicotine-specific scFv antibodies were sequenced as described (see application PCT/EP2007/061570), including clones F018, F063, J004, J042, N049, I022 and N038 (see Table 2).

TABLE 2

SEQ ID NOs of nucleic acid sequences and amino acid sequences of nicotine specific scFv antibodies.

| scFv | Nucleic Acid Sequence | Amino Acid Sequence |
|---|---|---|
| F018 | 59 | 60 |
| F063 | 61 | 62 |
| J004 | 63 | 64 |
| J042 | 65 | 66 |
| N049 | 67 | 68 |
| I022 | 69 | 70 |
| N038 | 71 | 72 |

Among these, all heavy chain variable regions comprised VH4 family sequences (SEQ ID NOs 24, 28, 33, 39, 43, and 47). The light chain variable regions comprised Vλ1 family sequences (SEQ ID NOs 26, 31, 35, 37, 41, and 49), with the exception of I022, which comprised a Vκ3 sequence (SEQ ID NO:45). Significantly, heavy and light chain variable regions of antibodies F018, F063, J004, J042 and N049 were very closely related to one another and differed only at few amino acid positions. The heavy chain variable regions of clones F063 and J042 were identical (SEQ ID NO:28). An overview over nucleic acid sequences and amino acid sequences comprised by the variable regions of nicotine binding antibodies is provided in Table 3.

TABLE 3

SEQ ID NOs of nucleic acid sequences and amino acid sequences comprised by HCVRs and LCVRs of nicotine specific antibodies.

| scFv | Nucleic Acid Sequence (HCVR)[1] | Amino Acid Sequence (HCVR) | Nucleic Acid Sequence (LCVR)[2] | Amino Acid Sequence (LCVR) |
|---|---|---|---|---|
| F018 | 23 | 24 | 25 | 26 |
| F063 | 27 | 28 | 30 | 31 |
| J004 | 32 | 33 | 34 | 35 |
| J042 | 29 | 28 | 36 | 37 |
| N049 | 38 | 39 | 40 | 41 |
| I022 | 42 | 43 | 44[3] | 45 |
| N038 | 46 | 47 | 48 | 49 |

[1] all HCVRs comprise VH4 sequences;
[2] all LCVRs except the LCVR of I022 comprise V lambda 1 sequences;
[3] LCVR of I022 comprises a V kappa 3 sequence;

Example 3

Expression and Purification of Nicotine-Specific scFv-Fc Fusion Proteins

Large-scale expression of scFv-Fc fusion proteins was done in HEK-293T cells. One day before transfection, $5 \times 10^6$ 293T cells were plated onto a 10 cm tissue culture plate for each protein to be expressed. Cells were then transfected with the respective scFv-Fc fusion construct using Lipofectamin Plus (Invitrogen) according to the manufacturer's recommendations, incubated one day, and replated on one 14 cm dish in the presence of 1 µg/ml puromycin. After 3 days of selection, puromycin-resistant cells were transferred to three Poly-L-Lysine coated 14 cm plates and grown to confluency. Medium was then replaced by serum-free medium and supernatants containing the respective scFv-Fc fusion protein was collected every 3 days and filtered through a 0.22 µM Millex GV sterile filter (Millipore).

For each of the scFv-Fc fusion proteins, the consecutive harvests were pooled and applied to a protein A-sepharose column. The column was washed with 10 column volumes of phosphate-buffered saline (PBS), and bound protein eluted with 0.1 M Glycine pH 3.6. 1 ml fractions were collected in tubes containing 0.1 ml of 1 M Tris pH 7.5 for neutralization. Protein-containing fractions were analyzed by SDS-PAGE and pooled. The buffer was exchanged with PBS by dialysis using 10'000 MWCO Slide-A-Lyzer dialysis cassettes (Pierce). The purified proteins in PBS were then filtered through 0.22 µM Millex GV sterile filters (Millipore) and aliquotted. Working stocks were kept at 4° C., whereas aliquots for long-term storage were flash-frozen in liquid nitrogen and kept −80° C.

Example 4

Verification of Nicotine-Specific Binding by Inhibition ELISA

To exclude possible linker specificity of the antibodies, binding to free Nicotine was verified by inhibition ELISA. Thus, ELISA plates were coated with Nicotine-conjugated RNAse at a concentration of 4 µg/ml in phosphate-buffered saline (PBS), over night at 4° C. The plates were then washed with wash buffer (PBS/0.05% Tween) and blocked for 2 h at room temperature with 3% BSA in wash buffer. The plates were then washed again and incubated with purified scFv-F018, scFv-F063, scFv-I022, scFv-J004, scFv-N038 and scFv-N049 at a concentration of 100 ng/ml in the absence or presence of increasing concentrations of free nicotine (0.1 to 100 µM). Plates were incubated at room temperature for 2 h and then extensively washed with wash buffer. Bound scFv-Fc fusion proteins were then detected by a 1 h incubation with a HRPO-labeled, Fcγ-specific, goat anti-human IgG antibody (Jackson ImmunoResearch Laboratories 109-035-098). After extensive washing with wash buffer, plates were developed with OPD solution (1 OPD tablet, 25 ml OPD buffer and 8 µl 30% $H_2O_2$) for 5 to 10 minutes and the reaction was stopped with 5% $H_2SO_4$ solution. Plates were then read at OD 450 nm on an ELISA reader (Biorad Benchmark). Binding of each of the antibodies to immobilized nicotine was efficiently inhibited by free nicotine, with IC50 values in the low micromolar range.

Example 5

Construction, Expression, and Purification of Human Nicotine-Specific IgG2

The heavy and light chain variable region coding segments of scFv-F018, scFv-F063, scFv-I022, scFv-J004, scFv-J042, scFv-N038 and scFv-N049 were amplified by PCR using variable region-specific transfer primers (disclosed as SEQ ID NOs 92 to 103 of application PCT/EP2007/061570). For example, the DNA encoding the light chain variable region of antibody F018 was amplified using the primers VL-Sac1-F4 (5'-CAG GCG GCC GAG ATC GAG CTC ACT CAG C-3') and VL-EcoR5-B1 (5'-ACC GCC GAG GAT ATC CAG CTG GGT-3'). The DNA encoding the heavy chain variable region was amplified with the primers VH-XhoI-F (5'-SAG GTG CAG CTG CTC GAG TCK GG-3') and VH-ApaI-B (5'-GCC ACT AGT GAC CGA TGG GCC-3'). The DNAs encoding the other light and heavy chain variable regions were amplified accordingly.

The resulting λ or κ light chain variable region PCR products were digested with the restriction enzymes SacI and EcoR5, purified by agarose gel electrophoresis, and ligated into SacI-EcoR5 digested pCMV-LC-λ or pCMV-LC-κ, respectively (disclosed as SEQ ID NOs 110 and 71 of application PCT/EP2007/061570). The resulting vectors allow for expression of complete human light chains, including the signal peptide, e.g. the F018 λ light chain (SEQ ID NO:56). Similarly, the heavy chain variable region PCR products were digested with the restriction enzymes XhoI and ApaI, gel purified, and ligated into XhoI-ApaI digested pCMV-HC-γ2 (disclosed as SEQ ID NO:78 of application PCT/EP2007/061570). The resulting vectors allow for expression of complete human γ2 heavy chains, including the signal peptide, e.g. the F018 γ2 heavy chain (SEQ ID NO:55).

Co-expression of each of the pCMV-LC-λ or -κ expression constructs with the corresponding pCMV-HC-γ2 expression construct in principle allows for the production of whole IgG2. However, to increase yields and facilitate large-scale production of antibodies, heavy and light chain coding regions were first combined into a single, EBNA-based expression vector, pCB15 (disclosed as SEQ ID NO:104 of application PCT/EP2007/061570). For instance, for expression of antibody F018 as a whole IgG2, the γ2 heavy chain coding region was excised from pCMV-F018-HC-γ2 by digestion with the restriction enzymes AscI and PacI, the resulting 1403 bp fragment purified by agarose gel electrophoresis, and then ligated into Asc1-Pac1 digested pCB15, yielding pCB15-F018-HC-γ2. The F018 λ light chain coding region was then excised from pCMV-F018-LC-λ by digestion with Nhe1 and Pme1, the resulting 723 bp fragment gel-purified, and then ligated into Nhe1-Pme1 digested pCB15-F018-HC-γ2, yielding the whole IgG expression vector pCB15-F018-IgG2λ. Expression of whole IgG was done in HEK-293T cells, exactly as described for the scFv-Fc fusion proteins (Example 2).

Example 6

Construction, Expression, and Purification of Fully Human Nicotine-Specific IgG2

The pCB15 expression vectors constructed as described in Example 4 direct the synthesis of whole IgG2 molecules that are largely human. However, compared to a fully human antibody, there are still two minor differences. First, the sequence of the heavy or light chain signal peptide is encoded by the expression vector and typically does not correspond to the native signal peptide of the variable region in question. Second, amino acid positions flanking the heavy or light chain variable region are predetermined by the vector, e.g. due to the presence of restriction sites. Thus, in order to generate fully human mAbs, these differences need to be corrected for each of the heavy and light chain expression vectors. For example, a vector directing expression of a fully human F018 γ2 heavy chain, including the native signal peptide (SEQ ID NO:57) was generated as follows. The F018 heavy chain variable region was first amplified by PCR from the plasmid pCMV-F018-HC-γ2 using the primers F018-HC-fh-F1 (5'-TTC CTC CTG TTG GTG GCA GCA CCC AGG TGG GTG CTG TCC CAG CTG CAA CTG CAG GAG TC-3') and F018-HC-fh-B1 (5'-GAC CGA TGG GCC CTT GGT GGA AGC-3'). The resulting PCR product was then further amplified using the primers F018-HC-fh-F2 (5'-GAG GGC GCG CCA CCA TGA AGC ACC TGT GGT TCT TCC TCC TGT TGG TGG CAG C-3') and F018-HC-fh-B1. The final PCR product was digested with the restriction enzymes AscI and ApaI, purified by agarose gel electrophoresis, and ligated into Asc1-Apa1 digested pCMV-HC-γ2, yielding the plasmid pCMV-fhF018-HC-γ2.

Similarly, a vector directing expression of a fully human F018 λ light chain including the native signal peptide (SEQ ID NO:58) was generated as follows. First, the F018 light chain variable region was amplified by PCR from pCMV-F018-LC-λ using the primers F018-LC-fh-F1 (5'-CCT CCT CAC CCT CCT CAC TCA CTG CGC CGG GTC CTG GGC CCA GTC TGT GCT CAC-3') and F018-LC-fh-B1 (5'-GGG CTG ACC TAG CAC GGT CAG CTG GGT GCC-3'). In parallel, the λ light chain was amplified using the primers F018-LC-fh-F3 (5'-GGC ACC CAG CTG ACC GTG CTA GGT CAG CCC-3') and T7 (5'-TAA TAC GAC TCA CTA TAG GG-3'). Second, the resulting PCR products were assembled by PCR using the primers F018-LC-fh-F2 (5'-GAG GCT AGC GCC ACC ATG GCC GGC TTC CCC CTC CTC CTC ACC CTC CTC ACT C-3') and T7. The final PCR product was digested with the restriction enzymes Nhe1 and Pme1, purified by agarose gel electrophoresis, and ligated into Nhe1-Pme1 digested pCMV-LC-κ, yielding the plasmid pCMV-fhF018-LC-λ.

The vector pCB15-fhF018-IgG2λ, directing the expression of a fully human mAb F018, was constructed by sequential cloning of heavy and light chain coding regions into pCB15, using the cloning strategy set forth in Example 4. Expression vectors directing expression of fully human mAbs F063, I022, J004, J042, N038 and N049 are constructed in a similar manner.

Example 7

Determination of Affinities by Equilibrium Dialysis

Affinity of antibodies for (S)-(−)-nicotine was determined by equilibrium dialysis using a DispoEquilibriumDialyzer (Harvard Biosciences). Two chambers of the dialyzer were separated by a membrane (10'000 Da cut-off). One chamber was filled with purified scFv-Fc or IgG2 at a concentration of 5.4 μg/ml or 7.5 μg/ml in PBS/2% BSA, respectively, whereas the other chamber did not contain antibody. Concentrations of tritium-labeled (S)-(−)-nicotine (Amersham) ranging from 3 to 444 nM were used. Equilibrium dialysis was allowed to proceed for 48-72 h. Aliquots from both sides of the chamber were taken and radioactivity measured in a scintillation counter. Radioactivity corresponding to antibody-bound (S)-(−)-nicotine was calculated by subtracting the radioactivity measured for the chamber containing no antibody from the one containing the antibody. The free (S)-(−)-nicotine concentration was determined from the radioactivity measured for the chamber containing no antibody. The equilibrium dissociation constant (Kd) was derived from the fit of a one-site binding model to the measured bound radioactivity as a function of the free (S)-(−)-nicotine concentration. Most nicotine-specific antibodies bound free (S)-(−)-nicotine with Kd values in the low nanomolar range (Table 4). The IgG2 antibodies had affinities comparable to the scFv-Fc, with Kd values that differed by no more than approximately 2-fold. The IgG2-F018 had a dissociation constant of 7 nM, almost 2-fold lower than the one measured for scFv-Fc-F018 and at least 4 times lower than the Kd of the other IgG2. It is noteworthy that the affinity of polyclonal antibodies against (S)-(−)-nicotine is in the range of 30-70 nM, i.e. considerably lower than the affinity of clone F018 (Maurer P. et al., 2005, Eur. J. Immunol. 35, 2031-2040).

TABLE 4

Dissociation constants Kd values (nM) measured by equilibrium dialysis.
Values shown are the mean ± SD of at least 2 independent experiments,
except for IgG2-N038, which was measured only once.

| format | F018 | F063 | I022 | J004 | J042 | N038 | N049 |
|---|---|---|---|---|---|---|---|
| scFv-Fc | 11.5 ± 1.5 | 70.5 ± 14 | 42.5 ± 17 | 33.3 ± 2 | 47.0 ± 3.1 | 686.3 ± 58 | 72.7 ± 5.6 |
| IgG2 | 7.4 ± 1.2 | 31.4 ± 13 | 89.9 ± 9.8 | 64.5 ± 2.2 | 30.2 ± 11 | 743.8 | 35.6 ± 3.5 |

Cross-reactivity of mAb IgG2-F018 to (−)-cotinine and acetylcholine was determined by co-incubation of 10 fold serial dilutions of these compounds (1 nM to 100 μM) with 56 nM tritium-labeled (S)-(−)-nicotine in the equilibrium dialysis chambers as described above (FIG. 1). As expected, unlabeled (−)-nicotine readily displaced tritium-labeled (S)-(−)-nicotine. In contrast, acetylcholine, which is structurally unrelated to nicotine but binds to the same binding pocket of the nicotinic acetylcholine receptor (Celie P. H. et al., 2004, Neuron 41, 907-914), did not interfere with (S)-(−)-nicotine binding even at a 4000 fold molar excess. Similarly, (−)-cotinine, which is the major metabolic product of (S)-(−)-nicotine and present in a 10-20 fold molar excess over nicotine in the blood of smokers (Benowitz N. L., 1997, Br. J. Clin. Pharmacol. 43, 259-267), did not effectively compete with (S)-(−)-nicotine for binding to IgG2-F018. Based on the IC50 observed, it can be estimated that IgG2-F018 binds (−)-cotinine about 1000 fold less strongly than (S)-(−)-nicotine. Therefore, the presence of a molar excess of (−)-cotinine in the blood of a smoker is unlikely to interfere with the therapeutic efficacy of IgG2-F018.

We next determined the affinities of mAbs IgG2-F018, -F063, J004, -J042 and -N049 for the (R)-(+)-isomer of nicotine. This stereoisomer is present in the tobacco plant. In addition, it can be formed by the combustion process during smoking and has qualitatively similar activities on the central nervous system as (S)-(−)-nicotine (Hukkanen J. et al., 2005, Pharmacol. Rev. 57, 79-115). Thus, the binding of a fixed concentration of tritium-labeled (S)-(−)-nicotine (F018: 56 nM; F063, J004, J042, N049: 111 nM) to each of the antibodies was measured by equilibrium dialysis in the presence of increasing concentrations of unlabeled (R)-(+)-nicotine (1 nM to 100 μM). The equilibrium dissociation constant (Kd) was derived from the fit of a one-site competition model to the measured bound radioactivity as a function of the (R)-(+)-nicotine concentration. Surprisingly, (R)-(+)-nicotine was highly efficient in competing with (S)-(−)-nicotine for binding to each of the antibodies, with Kd values that were about 2 to 5 fold lower than those of (S)-(−)-nicotine (Table 5).

TABLE 5

Dissociation constants Kd (nM) of antibody-(R)-(+)-nicotine interactions measured by equilibrium dialysis.

| format | F018 | F063 | J004 | J042 | N049 |
|---|---|---|---|---|---|
| IgG2 | 3.1 | 6.6 | 12.6 | 7.7 | 10.5 |

Example 8

Evaluation of Nicotine Distribution in Plasma and Brain in Mice

Groups of 5 to 6 female Balb/c mice were injected i.p. with 0.1 to 3 mg of each of the recombinant human IgG2 monoclonal antibodies. One day later, inhibition of nicotine entry into the brain was analyzed by intravenous injection of tritium-labelled (S)-(−)-nicotine (Amersham) (375, 750 or 1500 ng) into the tail vein. Mice were sacrificed 5 min later by $CO_2$ asphyxiation and blood and brain were collected. Nicotine concentrations in serum and brain were calculated from the radioactivity present. Brain nicotine concentration was corrected for the blood content of brain (3 μl/100 mg). The percent reduction of nicotine uptake into the brain was calculated relative to the nicotine concentrations found in brains of mice injected with control IgG. With all nicotine-specific antibodies tested, a reduction in the distribution of nicotine to the brain was observed. With most antibodies, the reduction observed at a dose of 0.5 mg per mouse was typically 40% or more. The most potent mAb under these experimental conditions was F018, which consistently reduced entry of nicotine to the brain by more than 60% (Tables 6 and 7).

TABLE 6

Inhibition of nicotine entry into brain of mice by nicotine-specific antibodies (passive immunization with 0.5 mg IgG2; challenge with 750 ng nicotine).

| antibody | brain nicotine (cpm/g) | % reduction |
| --- | --- | --- |
| control IgG | 131559 ± 14650 | — |
| F018 | 46717 ± 3550 | 64 |
| J004 | 77002 ± 9293 | 41 |
| J042 | 72678 ± 7423 | 45 |
| N049 | 68395 ± 2885 | 48 |

TABLE 7

Inhibition of nicotine entry into brain of mice by nicotine-specific antibodies (passive immunization with 0.5 mg IgG2; challenge with 750 ng nicotine).

| antibody | brain nicotine (cpm/g) | % reduction |
| --- | --- | --- |
| control IgG | 114048 ± 13786 | — |
| F018 | 42803 ± 3751 | 62 |
| F063 | 54783 ± 3909 | 52 |
| I022 | 68687 ± 5498 | 40 |
| N038 | 91823 ± 14311 | 19 |

Example 9

Use of the Heavy Chain Variable Region of Anti-Nicotine Antibody F018 to Identify a Complementary Light Chain Variable Region ("Chain Shuffling")

The nucleotide sequence of all primers used in the present example, and for which no sequence is provided herein can be found under the identical designation in: Phage Display—A Laboratory Manual, Cold Spring Harbor Laboratory Press, 2001, Protocol 9.2.

The DNA sequence encoding the heavy chain variable region of antibody F018 is amplified by PCR from a DNA molecule comprising the scFv-F018 sequence (SEQ ID NO:59) using the primers HSCVH35-FL and HSC-F018-B (5'-CCT GGC CGG CCT GGC CAC TAG TGA CCG ATG GGC CCT TGG TGG AAG C-3', SEQ ID NO:86). A library of DNA sequences encoding human κ light chain variable regions is amplified by PCR from the cDNA of B cells from a human subject immunized with a Nicotine-carrier conjugate, using an equimolar mix of the 4 sense primers HSCK1-F, HSCK24-F, HSCK3-F and HSCK5-F, plus an equimolar mix of the 4 antisense primers HSCJK14o-B, HSCJK2o-B, HSCJK3o-B and HSCJK5o-B. A library of DNA sequences encoding human λ light chain variable regions is amplified by PCR from the cDNA of B cells from a human subject immunized with a Nicotine-carrier conjugate, using an equimolar mix of the 9 sense primers HSCLam1a, HSCLam1b, HSCLam2, HSCLam3, HSCLam4, HSCLam6, HSCLam78, HSCLam9 and HSCLam10, plus an equimolar mix of 3 antisense primers HSCJLam1236, HSCJLam4 and HSCJLam57.

For selection of complementary light chain variable regions, scFv coding regions are assembled by PCR overlap extension of the F018 VH PCR product with either the Vκ library PCR product or the Vλ library PCR product using the primers RSC-F and RSC-B. The resulting ~750-800 bp PCR products encode a 5' light chain variable region library (either κ or λ) and the 3' heavy chain variable region of Nicotine-specific antibody F018, linked by an 18 amino acid flexible linker, and flanked by two SfiI restriction sites. The scFv-κ and -λ library fragments are pooled in equimolar ratio, digested with the restriction endonuclease SfiI, and cloned into the vector pDel-SP-TM for screening by Sindbis-based scFv cell surface display essentially as described in Example 1. Alternatively, the SfiI-digested scFv library fragments are cloned into SfiI-digested pComb3H (Rader C, Barbas CF 3rd., 1997, Curr Opin Biotechnol. 8, 503-508). Antibodies are then expressed and selected for binding to immobilized RNAse-Nicotine conjugate by phage display using procedures described (Phage Display: A Laboratory Manual, Cold Spring Harbor Laboratory Press, 2001).

The invention claimed is:

1. An isolated monoclonal antibody specifically binding nicotine, wherein said monoclonal antibody is a human monoclonal antibody, and
   (a) wherein said monoclonal antibody comprises at least one heavy chain variable region (HCVR), wherein said HCVR comprises:
      (i) one heavy chain complementarity determining region (HC CDR)1, wherein said HC CDR1 comprises the peptide of SEQ ID NO:1;
      (ii) one HC CDR2, wherein said HC CDR2 comprises the peptide of SEQ ID NO:2; and
      (iii) one HC CDR3, wherein said HC CDR3 comprises the peptide of any one of SEQ ID NOs 3 and 4; and
   (b) wherein said monoclonal antibody comprises at least one light chain variable region (LCVR), wherein said LCVR comprises:
      (i) one light chain complementarity determining region (LC CDR)1, wherein said LC CDR1 comprises the peptide of any one of SEQ ID NOs 5, 6, and 7;
      (ii) one LC CDR2, wherein said LC CDR2 comprises the peptide of SEQ ID NO:8;
      (iii) one LC CDR3, wherein said LC CDR3 comprises the peptide of any one of SEQ ID NOs 9 and 10.

2. The monoclonal antibody of claim 1, wherein:
   (a) said HCVR comprises a peptide selected from SEQ ID NOs 24, 28, 33, and 39; and
   (b) wherein said LCVR comprises a peptide selected from SEQ ID NOs 26, 31, 35, 37, and 41.

3. The monoclonal antibody of claim 1, wherein:
   (a) said HCVR comprises the peptide of SEQ ID NO:24, and wherein said LCVR comprises the peptide of SEQ ID NO:26;
   (b) said HCVR comprises the peptide of SEQ ID NO:28, and wherein said LCVR comprises the peptide of SEQ ID NO:31;
   (c) said HCVR comprises the peptide of SEQ ID NO:33, and wherein said LCVR comprises the peptide of SEQ ID NO:35;
   (d) said HCVR comprises the peptide of SEQ ID NO:28, and wherein said LCVR comprises the peptide of SEQ ID NO:37; or
   (e) said HCVR comprises the peptide of SEQ ID NO:39, and wherein said LCVR comprises the peptide of SEQ ID NO:41.

4. The monoclonal antibody of claim 1, wherein said monoclonal antibody comprises at least one gamma 2 heavy chain and at least one lambda light chain, wherein
   (a) said gamma 2 heavy chain comprises the peptide of SEQ ID NO:73, and wherein said lambda light chain comprises the peptide of SEQ ID NO:74;
   (b) said gamma 2 heavy chain comprises the peptide of SEQ ID NO:75, and wherein said lambda light chain comprises the peptide of SEQ ID NO:76;
   (c) said gamma 2 heavy chain comprises the peptide of SEQ ID NO:77, and wherein said lambda light chain comprises the peptide of SEQ ID NO:78;
   (d) said gamma 2 heavy chain comprises the peptide of SEQ ID NO:75, and wherein said lambda light chain comprises the peptide of SEQ ID NO:79; or
   (e) said gamma 2 heavy chain comprises the peptide of SEQ ID NO:80, and wherein said lambda light chain comprises the peptide of SEQ ID NO:81.

5. The monoclonal antibody of claim 1, wherein said monoclonal antibody is an IgG2.

6. The monoclonal antibody of claim 1, wherein said monoclonal antibody is specifically binding (S)-(−)-nicotine and (R)-(+)-nicotine.

7. The monoclonal antibody of claim 1, wherein said monoclonal antibody is binding (S)-(−)-nicotine and (R)-(+)-nicotine, wherein the dissociation constant Kd of said binding of said monoclonal antibody to said (S)-(−)-nicotine is 1 to 100 nM.

8. The monoclonal antibody of claim 1, wherein HC CDR 3 comprises the peptide of SEQ ID NO:3, and wherein said LC CDR1 comprises the peptide of SEQ ID NO:5, and wherein said LC CDR3 comprises the peptide of SEQ ID NO:9.

9. The monoclonal antibody of claim 2, wherein said HCVR comprises the peptide of SEQ ID NO:24, or wherein said LCVR comprises the peptide of SEQ ID NO:26.

10. The monoclonal antibody of claim 1, wherein said HCVR comprises the peptide of SEQ ID NO:24, and wherein said LCVR comprises the peptide of SEQ ID NO:26.

11. The monoclonal antibody of claim 1, wherein said monoclonal antibody comprises at least one gamma 2 heavy chain and at least one lambda light chain, wherein said gamma 2 heavy chain comprises the peptide of SEQ ID NO:73, and wherein said lambda light chain comprises the peptide of SEQ ID NO:74.

12. The monoclonal antibody of claim 1, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 0.1 to 10 nM; and wherein the dissociation constant Kd of said binding of said monoclonal antibody to said (R)-(+)-nicotine is 0.1 to 10 nM; and wherein said monoclonal antibody comprises a gamma 2 heavy chain and a lambda light chain, wherein said gamma 2 heavy chain comprises the peptide of SEQ ID NO:73, and wherein said lambda light chain comprises the peptide of SEQ ID NO:74.

13. The monoclonal antibody of claim 1, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 10 to 100 nM; and wherein the dissociation constant Kd of said binding of said monoclonal antibody to said (R)-(+)-nicotine is 0.1 to 10 nM; and wherein said monoclonal antibody comprises a gamma 2 heavy chain and a lambda light chain, wherein said gamma 2 heavy chain comprises the peptide of SEQ ID NO:75, and wherein said lambda light chain comprises the peptide of SEQ ID NO:76.

14. The monoclonal antibody of claim 1, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 10 to 100 nM, and wherein the dissociation constant Kd of said binding of said monoclonal antibody to said (R)-(+)-nicotine is 1 to 20 nM; and wherein said monoclonal antibody comprises a gamma 2 heavy chain and a lambda light chain, wherein said gamma 2 heavy chain comprises the peptide of SEQ ID NO:77, and wherein said lambda light chain comprises the peptide of SEQ ID NO:78.

15. The monoclonal antibody of claim 1, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 20 to 60 nM; and wherein the dissociation constant Kd of said binding of said monoclonal antibody to said (R)-(+)-nicotine is 0.1 to 10 nM; wherein said monoclonal antibody comprises a gamma 2 heavy chain and a lambda light chain, wherein said gamma 2 heavy chain comprises the peptide of SEQ ID NO:75, and wherein said lambda light chain comprises the peptide of SEQ ID NO:79.

16. The monoclonal antibody of claim 1, wherein said monoclonal antibody is a human monoclonal antibody, and wherein said monoclonal antibody is binding (S)-(−)-nicotine and (R)-(+)-nicotine, wherein the dissociation constant Kd of said binding of said monoclonal antibody to said (S)-(−)-nicotine is 20 to 80 nM; and wherein the dissociation constant Kd of said binding of said monoclonal antibody to said (R)-(+)-nicotine is 0.1 to 15 nM; wherein said monoclonal antibody comprises a gamma 2 heavy chain and a lambda light chain, wherein said gamma 2 heavy chain comprises the peptide of SEQ ID NO:80, and wherein said lambda light chain comprises the peptide of SEQ ID NO:81.

17. A method of passive immunization against nicotine, said method comprising administering to a subject an effective amount of the monoclonal antibody of claim 1.

18. The method of claim 17, wherein said subject is a human.

19. A method of treating of nicotine addiction, said method comprising administering to a subject an effective amount of the monoclonal antibody of claim 1.

20. The method of claim 19, wherein said subject is a human.

\* \* \* \* \*

SEQUENCE LISTING

<160> NUMBER OF SEQ ID NOS: 86

<210> SEQ ID NO 1
<211> LENGTH: 4
<212> TYPE: PRT
<213> ORGANISM: Homo sapiens

<400> SEQUENCE: 1

Gly Gly Ser Ile
1

<210> SEQ ID NO 2
<211> LENGTH: 7
<212> TYPE: PRT
<213> ORGANISM: Homo sapiens

<400> SEQUENCE: 2

Ile Tyr Ser Ser Gly Ser Thr
1               5

<210> SEQ ID NO 3

```
<211> LENGTH: 15
<212> TYPE: PRT
<213> ORGANISM: Homo sapiens

<400> SEQUENCE: 3

Val Ala Trp Phe Gly Asp Leu Leu Ser Leu Lys Gly Val Glu Leu
1               5                   10                  15

<210> SEQ ID NO 4
<211> LENGTH: 15
<212> TYPE: PRT
<213> ORGANISM: Homo sapiens

<400> SEQUENCE: 4

Val Val Trp Phe Gly Asp Leu Leu Ser Leu Lys Gly Val Glu Leu
1               5                   10                  15

<210> SEQ ID NO 5
<211> LENGTH: 8
<212> TYPE: PRT
<213> ORGANISM: Homo sapiens

<400> SEQUENCE: 5

Ser Ser Asn Ile Gly Ser Asn Tyr
1               5

<210> SEQ ID NO 6
<211> LENGTH: 8
<212> TYPE: PRT
<213> ORGANISM: Homo sapiens

<400> SEQUENCE: 6

Ser Ser Asn Ile Gly Ser Lys Asn
1               5

<210> SEQ ID NO 7
<211> LENGTH: 8
<212> TYPE: PRT
<213> ORGANISM: Homo sapiens

<400> SEQUENCE: 7

Ser Ser Asn Ile Gly Ser Ser Tyr
1               5

<210> SEQ ID NO 8
<211> LENGTH: 3
<212> TYPE: PRT
<213> ORGANISM: Homo sapiens

<400> SEQUENCE: 8

Arg Asn Asn
1

<210> SEQ ID NO 9
<211> LENGTH: 11
<212> TYPE: PRT
<213> ORGANISM: Homo sapiens

<400> SEQUENCE: 9

Ala Ala Trp Asp Asp Ser Leu Ser Ala Trp Val
1               5                   10

<210> SEQ ID NO 10
<211> LENGTH: 11
<212> TYPE: PRT
<213> ORGANISM: Homo sapiens
```

```
<400> SEQUENCE: 10

Ala Ala Trp Asp Asp Ser Leu Ser Gly Trp Val
1               5                   10

<210> SEQ ID NO 11
<211> LENGTH: 10
<212> TYPE: PRT
<213> ORGANISM: Homo sapiens

<400> SEQUENCE: 11

Gly Gly Ser Ile Ser Ser Thr Ser Tyr Tyr
1               5                   10

<210> SEQ ID NO 12
<211> LENGTH: 7
<212> TYPE: PRT
<213> ORGANISM: Homo sapiens

<400> SEQUENCE: 12

Ile Ser Tyr Ser Gly Ser Thr
1               5

<210> SEQ ID NO 13
<211> LENGTH: 13
<212> TYPE: PRT
<213> ORGANISM: Homo sapiens

<400> SEQUENCE: 13

Ala Arg Ile Leu Trp Phe Gly Glu Tyr Leu Gly Asp Tyr
1               5                   10

<210> SEQ ID NO 14
<211> LENGTH: 6
<212> TYPE: PRT
<213> ORGANISM: Homo sapiens

<400> SEQUENCE: 14

Gln Ser Val Ser Asn Tyr
1               5

<210> SEQ ID NO 15
<211> LENGTH: 3
<212> TYPE: PRT
<213> ORGANISM: Homo sapiens

<400> SEQUENCE: 15

Gly Ala Ser
1

<210> SEQ ID NO 16
<211> LENGTH: 9
<212> TYPE: PRT
<213> ORGANISM: Homo sapiens

<400> SEQUENCE: 16

Gln Gln Tyr Tyr Ser Thr Pro Trp Thr
1               5

<210> SEQ ID NO 17
<211> LENGTH: 9
<212> TYPE: PRT
<213> ORGANISM: Homo sapiens

<400> SEQUENCE: 17
```

<210> SEQ ID NO 18
<211> LENGTH: 7
<212> TYPE: PRT
<213> ORGANISM: Homo sapiens

<400> SEQUENCE: 18

Ser Asn His Ser Gly Ser Thr
1               5

<210> SEQ ID NO 19
<211> LENGTH: 14
<212> TYPE: PRT
<213> ORGANISM: Homo sapiens

<400> SEQUENCE: 19

Ala Arg Glu Ala Gly Tyr Ser Ser Ser Trp Tyr Phe Asp Tyr
1               5                   10

<210> SEQ ID NO 20
<211> LENGTH: 8
<212> TYPE: PRT
<213> ORGANISM: Homo sapiens

<400> SEQUENCE: 20

Ser Ser Asn Ile Gly Asn Asn Tyr
1               5

<210> SEQ ID NO 21
<211> LENGTH: 3
<212> TYPE: PRT
<213> ORGANISM: Homo sapiens

<400> SEQUENCE: 21

Asp Asn Asn
1

<210> SEQ ID NO 22
<211> LENGTH: 11
<212> TYPE: PRT
<213> ORGANISM: Homo sapiens

<400> SEQUENCE: 22

Gly Thr Trp Asp Ser Ser Leu Ser Ala Trp Val
1               5                   10

<210> SEQ ID NO 23
<211> LENGTH: 333
<212> TYPE: DNA
<213> ORGANISM: Homo sapiens

<400> SEQUENCE: 23
tctggcccag gactggtgaa gccttcggag accctgtccc tcacctgcac tgtctctggt      60
ggctccatct ggggctggat ccgccagccc cagggaagg gctgagtg gattgggagt       120 atctattcta gtgggagcac ctactacaac ccgtccctca gagtcgagt caccacatcc      180 gtagacacgt ccaagaacca gttctccctg aggctgagct ctgtgaccgc cgcagacacg      240
gctgtgtatt actgtgtggc gtggttcggg gacttattat cgttgaaggg ggttgaattg      300
tggggccagg gaaccctggt caccgtctcc tca                                  333

<210> SEQ ID NO 24

<211> LENGTH: 111
<212> TYPE: PRT
<213> ORGANISM: Homo sapiens

<400> SEQUENCE: 24

```
Ser Gly Pro Gly Leu Val Lys Pro Ser Glu Thr Leu Ser Leu Thr Cys
1               5                   10                  15

Thr Val Ser Gly Gly Ser Ile Trp Gly Trp Ile Arg Gln Pro Pro Gly
            20                  25                  30

Lys Gly Leu Glu Trp Ile Gly Ser Ile Tyr Ser Ser Gly Ser Thr Tyr
        35                  40                  45

Tyr Asn Pro Ser Leu Lys Ser Arg Val Thr Thr Ser Val Asp Thr Ser
    50                  55                  60

Lys Asn Gln Phe Ser Leu Arg Leu Ser Ser Val Thr Ala Ala Asp Thr
65                  70                  75                  80

Ala Val Tyr Tyr Cys Val Ala Trp Phe Gly Asp Leu Leu Ser Leu Lys
                85                  90                  95

Gly Val Glu Leu Trp Gly Gln Gly Thr Leu Val Thr Val Ser Ser
            100                 105                 110
```

<210> SEQ ID NO 25
<211> LENGTH: 309
<212> TYPE: DNA
<213> ORGANISM: Homo sapiens

<400> SEQUENCE: 25

```
actcagccac cttcagcgtc tgggacccccc gggcagaggg tcaccatctc ttgttctgga      60
agcagctcca acatcggaag taattatgta tactggtacc agcagctccc aggaacggcc     120
cccaaactcc tcatctatag gaataatcag cggccctcag gggtccctga ccgattctct     180
ggctccaagt ctggcacctc agcctccctg gccatcagtg ggctccggtc cgaggatgag     240
gctgattatt actgtgcagc atgggatgac agcctgagtg cttgggtgtt cggcggaggc     300
acccagctg                                                              309
```

<210> SEQ ID NO 26
<211> LENGTH: 103
<212> TYPE: PRT
<213> ORGANISM: Homo sapiens

<400> SEQUENCE: 26

```
Thr Gln Pro Pro Ser Ala Ser Gly Thr Pro Gly Gln Arg Val Thr Ile
1               5                   10                  15

Ser Cys Ser Gly Ser Ser Ser Asn Ile Gly Ser Asn Tyr Val Tyr Trp
            20                  25                  30

Tyr Gln Gln Leu Pro Gly Thr Ala Pro Lys Leu Leu Ile Tyr Arg Asn
        35                  40                  45

Asn Gln Arg Pro Ser Gly Val Pro Asp Arg Phe Ser Gly Ser Lys Ser
    50                  55                  60

Gly Thr Ser Ala Ser Leu Ala Ile Ser Gly Leu Arg Ser Glu Asp Glu
65                  70                  75                  80

Ala Asp Tyr Tyr Cys Ala Ala Trp Asp Asp Ser Leu Ser Ala Trp Val
                85                  90                  95

Phe Gly Gly Gly Thr Gln Leu
            100
```

<210> SEQ ID NO 27
<211> LENGTH: 333
<212> TYPE: DNA

<213> ORGANISM: Homo sapiens

<400> SEQUENCE: 27

```
tctggcccag gactggtgaa gccttcggag accctgtccc tcacctgcac tgtctctggt      60
ggctccatct ggggctggat ccgccagccc cagggaagg  ggctggagtg gattgggagt     120
atctattcta gtgggagcac ctactacaac ccgtccctca agagtcgagt caccatatcc     180
gtagacacgt ccaagaacca gttctccctg aggctgagct ctgtgaccgc cgcagacacg     240
gctgtgtatt actgtgtggt gtggttcggg gacttattat cgttgaaggg ggtcgaattg     300
tggggccagg gaaccctggt caccgtctcc tca                                  333
```

<210> SEQ ID NO 28
<211> LENGTH: 111
<212> TYPE: PRT
<213> ORGANISM: Homo sapiens

<400> SEQUENCE: 28

```
Ser Gly Pro Gly Leu Val Lys Pro Ser Glu Thr Leu Ser Leu Thr Cys
1               5                   10                  15
Thr Val Ser Gly Gly Ser Ile Trp Gly Trp Ile Arg Gln Pro Pro Gly
            20                  25                  30
Lys Gly Leu Glu Trp Ile Gly Ser Ile Tyr Ser Ser Gly Ser Thr Tyr
        35                  40                  45
Tyr Asn Pro Ser Leu Lys Ser Arg Val Thr Ile Ser Val Asp Thr Ser
    50                  55                  60
Lys Asn Gln Phe Ser Leu Arg Leu Ser Ser Val Thr Ala Ala Asp Thr
65                  70                  75                  80
Ala Val Tyr Tyr Cys Val Val Trp Phe Gly Asp Leu Leu Ser Leu Lys
                85                  90                  95
Gly Val Glu Leu Trp Gly Gln Gly Thr Leu Val Thr Val Ser Ser
            100                 105                 110
```

<210> SEQ ID NO 29
<211> LENGTH: 333
<212> TYPE: DNA
<213> ORGANISM: Homo sapiens

<400> SEQUENCE: 29

```
tcgggcccag gactggtgaa gccttcggag accctgtccc tcacctgcac tgtctctggt      60
ggctccatct ggggctggat ccgccagccc cagggaagg  ggctggagtg gattgggagt     120
atctattcta gtgggagcac ctactacaac ccgtccctca agagtcgagt caccatatcc     180
gtagacacgt ccaagaacca gttctccctg aggctgagct ctgtgaccgc cgcagacacg     240
gctgtgtatt actgtgtggt gtggttcggg gacttattat cgttgaaggg ggttgaattg     300
tggggccagg gaaccctggt caccgtctcc tca                                  333
```

<210> SEQ ID NO 30
<211> LENGTH: 309
<212> TYPE: DNA
<213> ORGANISM: Homo sapiens

<400> SEQUENCE: 30

```
actcagccac cctcagtgtc tgggacccc  gggcagaggg tcaccgtctc ttgttctgga      60
agcagctcta acatcggaag taaaaatgta tactggtacc agcagctccc aggaacggcc     120
cccaaactcc tcatctatag gaataatcag cggccctcag ggtccctga  ccgattctct     180
ggctccaagt ctggcacctc agcctccctg gccatcagtg gctccggtc  cgaggatgag     240
```

```
gctgattatt actgtgcagc atgggatgac agcctgagtg gttgggtgtt cagcggaggc    300
accaaggtg                                                             309
```

<210> SEQ ID NO 31
<211> LENGTH: 103
<212> TYPE: PRT
<213> ORGANISM: Homo sapiens

<400> SEQUENCE: 31

```
Thr Gln Pro Pro Ser Val Ser Gly Thr Pro Gly Gln Arg Val Thr Val
1               5                   10                  15

Ser Cys Ser Gly Ser Ser Ser Asn Ile Gly Ser Lys Asn Val Tyr Trp
                20                  25                  30

Tyr Gln Gln Leu Pro Gly Thr Ala Pro Lys Leu Leu Ile Tyr Arg Asn
            35                  40                  45

Asn Gln Arg Pro Ser Gly Val Pro Asp Arg Phe Ser Gly Ser Lys Ser
        50                  55                  60

Gly Thr Ser Ala Ser Leu Ala Ile Ser Gly Leu Arg Ser Glu Asp Glu
65                  70                  75                  80

Ala Asp Tyr Tyr Cys Ala Ala Trp Asp Asp Ser Leu Ser Gly Trp Val
                85                  90                  95

Phe Ser Gly Gly Thr Lys Val
            100
```

<210> SEQ ID NO 32
<211> LENGTH: 333
<212> TYPE: DNA
<213> ORGANISM: Homo sapiens

<400> SEQUENCE: 32

```
tctggcccag gactggtgaa gccttcggag accctgtccc acacctgcac tgtctctggt    60
ggctccatct ggggctggat ccgccagccc ccagggaagg ggctggagtg gattgggagt    120
atctattcta gtgggagcac ctactacaac ccgtccctca agagtcgagt caccatatcc    180
gtagacacgt ccaagaacca gttctccctg aggctgagct ctgtgaccgc cgcagacacg    240
gctgtgtatt actgtgtggt gtggttcggg gacttattat cgttgaaggg ggttgaattg    300
tggggccagg gaaccctggt caccgtctcc tca                                 333
```

<210> SEQ ID NO 33
<211> LENGTH: 111
<212> TYPE: PRT
<213> ORGANISM: Homo sapiens

<400> SEQUENCE: 33

```
Ser Gly Pro Gly Leu Val Lys Pro Ser Glu Thr Leu Ser His Thr Cys
1               5                   10                  15

Thr Val Ser Gly Gly Ser Ile Trp Gly Trp Ile Arg Gln Pro Pro Gly
                20                  25                  30

Lys Gly Leu Glu Trp Ile Gly Ser Ile Tyr Ser Ser Gly Ser Thr Tyr
            35                  40                  45

Tyr Asn Pro Ser Leu Lys Ser Arg Val Thr Ile Ser Val Asp Thr Ser
        50                  55                  60

Lys Asn Gln Phe Ser Leu Arg Leu Ser Ser Val Thr Ala Ala Asp Thr
65                  70                  75                  80

Ala Val Tyr Tyr Cys Val Val Trp Phe Gly Asp Leu Leu Ser Leu Lys
                85                  90                  95
```

Gly Val Glu Leu Trp Gly Gln Gly Thr Leu Val Thr Val Ser Ser
            100                 105                 110

<210> SEQ ID NO 34
<211> LENGTH: 309
<212> TYPE: DNA
<213> ORGANISM: Homo sapiens

<400> SEQUENCE: 34
acgcagccgc cctcagtgtc tgggaccccc gggcagaggg tcaccatctc ttgttctgga     60
agcagctcca acatcggaag tagttatgta tactggtacc agcagctccc aggaacggcc    120
cccaaactcc tcatctatag gaataatcag cggccctcag gggtccctga ccgattctct    180
ggctccaagt ctggcacctc agcctccctg gccatcagtg gctccggtc cgaggatgag    240 gctgattatt actgtgcagc atgggatgac agcctgagtg gttgggtgtt cggcggaggc    300
accgagctg                                                             309

<210> SEQ ID NO 35
<211> LENGTH: 103
<212> TYPE: PRT
<213> ORGANISM: Homo sapiens

<400> SEQUENCE: 35

Thr Gln Pro Pro Ser Val Ser Gly Thr Pro Gly Gln Arg Val Thr Ile
1               5                   10                  15

Ser Cys Ser Gly Ser Ser Ser Asn Ile Gly Ser Ser Tyr Val Tyr Trp
            20                  25                  30

Tyr Gln Gln Leu Pro Gly Thr Ala Pro Lys Leu Leu Ile Tyr Arg Asn
        35                  40                  45

Asn Gln Arg Pro Ser Gly Val Pro Asp Arg Phe Ser Gly Ser Lys Ser
    50                  55                  60

Gly Thr Ser Ala Ser Leu Ala Ile Ser Gly Leu Arg Ser Glu Asp Glu
65                  70                  75                  80

Ala Asp Tyr Tyr Cys Ala Ala Trp Asp Asp Ser Leu Ser Gly Trp Val
                85                  90                  95

Phe Gly Gly Gly Thr Glu Leu
            100

<210> SEQ ID NO 36
<211> LENGTH: 309
<212> TYPE: PRT
<213> ORGANISM: Homo sapiens

<400> SEQUENCE: 36

Ala Cys Cys Cys Ala Gly Gly Ala Gly Cys Cys Cys Thr Cys Ala Gly
1               5                   10                  15

Thr Gly Thr Cys Thr Gly Gly Gly Ala Cys Cys Cys Cys Gly Gly Gly
            20                  25                  30

Gly Cys Ala Gly Ala Gly Gly Gly Thr Cys Ala Cys Cys Ala Thr Cys
        35                  40                  45

Thr Cys Thr Thr Gly Thr Thr Cys Thr Gly Gly Ala Ala Gly Cys Ala
    50                  55                  60

Gly Cys Thr Cys Cys Ala Ala Cys Ala Thr Cys Gly Gly Ala Ala Gly
65                  70                  75                  80

Thr Ala Ala Thr Thr Ala Thr Gly Thr Ala Thr Ala Cys Thr Gly Gly
                85                  90                  95

Thr Ala Cys Cys Ala Gly Cys Ala Gly Cys Thr Cys Cys Cys Ala Gly
            100                 105                 110

```
Gly Ala Ala Cys Gly Gly Cys Cys Cys Cys Ala Ala Cys Thr
            115                 120                 125
Cys Cys Thr Cys Ala Thr Cys Thr Ala Thr Ala Gly Gly Ala Thr
130                 135                 140
Ala Ala Thr Cys Ala Cys Gly Gly Cys Cys Thr Cys Ala Gly
145                 150                 155                 160
Gly Gly Gly Cys Cys Cys Thr Gly Ala Cys Cys Gly Ala Thr Thr
                165                 170                 175
Cys Thr Cys Thr Gly Gly Cys Thr Cys Cys Ala Ala Gly Thr Cys Thr
                180                 185                 190
Gly Gly Cys Ala Cys Cys Thr Cys Ala Gly Cys Cys Thr Cys Cys
            195                 200                 205
Thr Gly Gly Cys Cys Ala Thr Cys Ala Gly Thr Gly Gly Cys Thr
            210                 215                 220
Cys Cys Gly Gly Thr Cys Gly Ala Gly Ala Thr Gly Ala Gly
225                 230                 235                 240
Gly Cys Thr Gly Ala Thr Thr Ala Thr Thr Ala Cys Thr Gly Thr Gly
                245                 250                 255
Cys Ala Gly Cys Ala Thr Gly Gly Gly Ala Thr Gly Ala Cys Ala Gly
            260                 265                 270
Cys Cys Thr Gly Ala Gly Thr Gly Gly Thr Gly Gly Gly Thr Gly
            275                 280                 285
Thr Thr Cys Gly Gly Cys Gly Gly Ala Gly Gly Gly Ala Cys Cys Ala
            290                 295                 300
Ala Gly Cys Thr Gly
305
```

<210> SEQ ID NO 37
<211> LENGTH: 103
<212> TYPE: PRT
<213> ORGANISM: Homo sapiens

<400> SEQUENCE: 37

```
Thr Gln Glu Pro Ser Val Ser Gly Thr Pro Gly Gln Arg Val Thr Ile
1               5                   10                  15
Ser Cys Ser Gly Ser Ser Ser Asn Ile Gly Ser Asn Tyr Val Tyr Trp
                20                  25                  30
Tyr Gln Gln Leu Pro Gly Thr Ala Pro Lys Leu Leu Ile Tyr Arg Asn
            35                  40                  45
Asn Gln Arg Pro Ser Gly Ala Pro Asp Arg Phe Ser Gly Ser Lys Ser
        50                  55                  60
Gly Thr Ser Ala Ser Leu Ala Ile Ser Gly Leu Arg Ser Glu Asp Glu
65                  70                  75                  80
Ala Asp Tyr Tyr Cys Ala Ala Trp Asp Asp Ser Leu Ser Gly Trp Val
                85                  90                  95
Phe Gly Gly Gly Thr Lys Leu
            100
```

<210> SEQ ID NO 38
<211> LENGTH: 333
<212> TYPE: DNA
<213> ORGANISM: Homo sapiens

<400> SEQUENCE: 38
tctggcccag gactggtgaa gccttcggag accctgtccc tcacctgcac tgtctctggt      60
ggttccatct ggggctggat ccgccagccc ccagggaagg ggctggagtg gattgggagt     120

```
atctattcta gtgggagcac ctactacaac ccgtccctca agagtcgagt caccatatcc    180
gtagacacgt ccgagaacca gttctccctg aggctgagct ctgtgaccgc cgcagacacg    240
gctgtgtatt actgtgtggt gtggttcggg gacttattat cgttgaaggg ggttgaattg    300
tggggccagg gaaccctggt caccgtctcc tca                                333
```

```
<210> SEQ ID NO 39
<211> LENGTH: 111
<212> TYPE: PRT
<213> ORGANISM: Homo sapiens

<400> SEQUENCE: 39

Ser Gly Pro Gly Leu Val Lys Pro Ser Glu Thr Leu Ser Leu Thr Cys
1               5                   10                  15

Thr Val Ser Gly Gly Ser Ile Trp Gly Trp Ile Arg Gln Pro Pro Gly
            20                  25                  30

Lys Gly Leu Glu Trp Ile Gly Ser Ile Tyr Ser Ser Gly Ser Thr Tyr
        35                  40                  45

Tyr Asn Pro Ser Leu Lys Ser Arg Val Thr Ile Ser Val Asp Thr Ser
    50                  55                  60

Glu Asn Gln Phe Ser Leu Arg Leu Ser Ser Val Thr Ala Ala Asp Thr
65                  70                  75                  80

Ala Val Tyr Tyr Cys Val Val Trp Phe Gly Asp Leu Leu Ser Leu Lys
                85                  90                  95

Gly Val Glu Leu Trp Gly Gln Gly Thr Leu Val Thr Val Ser Ser
            100                 105                 110
```

```
<210> SEQ ID NO 40
<211> LENGTH: 309
<212> TYPE: DNA
<213> ORGANISM: Homo sapiens

<400> SEQUENCE: 40
actcagccac ccacagtgtc tgggaccccc gggcagaggg tcaccatctc ttgttctgga    60
agcagctcca acatcggaag taaaaatgta tactggtacc agcagctccc aggaacggcc    120
cccaaactcc tcatctatag gaataatcag cggccctcag gggtccctga ccgattctct    180
ggctccaagt ctggcaccct cagcctccct gccatcagtg gctccggtc cgaggatgag    240 gctgattatt actgtgcagc atgggatgac agcctgagtg gttgggtgtt cggcggaggc    300
accaaggtg                                                           309
```

```
<210> SEQ ID NO 41
<211> LENGTH: 103
<212> TYPE: PRT
<213> ORGANISM: Homo sapiens

<400> SEQUENCE: 41

Thr Gln Pro Pro Thr Val Ser Gly Thr Pro Gly Gln Arg Val Thr Ile
1               5                   10                  15

Ser Cys Ser Gly Ser Ser Ser Asn Ile Gly Ser Lys Asn Val Tyr Trp
            20                  25                  30

Tyr Gln Gln Leu Pro Gly Thr Ala Pro Lys Leu Leu Ile Tyr Arg Asn
        35                  40                  45

Asn Gln Arg Pro Ser Gly Val Pro Asp Arg Phe Ser Gly Ser Lys Ser
    50                  55                  60

Gly Thr Ser Ala Ser Leu Ala Ile Ser Gly Leu Arg Ser Glu Asp Glu
65                  70                  75                  80
```

Ala Asp Tyr Tyr Cys Ala Ala Trp Asp Asp Ser Leu Ser Gly Trp Val
            85                  90                  95

Phe Gly Gly Gly Thr Lys Val
            100

<210> SEQ ID NO 42
<211> LENGTH: 345
<212> TYPE: DNA
<213> ORGANISM: Homo sapiens

<400> SEQUENCE: 42
tcgggcccag gactggtgaa gccttcggag accctgtccc tcacctgcac tgtctctggt    60
ggctccatca gcagtactag ttactactgg ggctggatcc gccagccccc agggaagggg    120
ctggagtgga ttgggagtat ctcttatagt gggagcacct actacaaccc gtccctcaag    180
agtcgagtca ccatatccgt agacacgtcc aagaaccagt tctccctgaa gctgacctct    240
gtgaccgccg cagacacggc tgtgtattac tgtgcgagga ctatatggtt cggagagtac    300
ctaggggact actggggcca gggaaccctg gtcaccgtct cctca                   345

<210> SEQ ID NO 43
<211> LENGTH: 115
<212> TYPE: PRT
<213> ORGANISM: Homo sapiens

<400> SEQUENCE: 43

Ser Gly Pro Gly Leu Val Lys Pro Ser Glu Thr Leu Ser Leu Thr Cys
1               5                   10                  15

Thr Val Ser Gly Gly Ser Ile Ser Ser Thr Ser Tyr Tyr Trp Gly Trp
            20                  25                  30

Ile Arg Gln Pro Pro Gly Lys Gly Leu Glu Trp Ile Gly Ser Ile Ser
        35                  40                  45

Tyr Ser Gly Ser Thr Tyr Tyr Asn Pro Ser Leu Lys Ser Arg Val Thr
    50                  55                  60

Ile Ser Val Asp Thr Ser Lys Asn Gln Phe Ser Leu Lys Leu Thr Ser
65                  70                  75                  80

Val Thr Ala Ala Asp Thr Ala Val Tyr Tyr Cys Ala Arg Ile Leu Trp
            85                  90                  95

Phe Gly Glu Tyr Leu Gly Asp Tyr Trp Gly Gln Gly Thr Leu Val Thr
            100                 105                 110

Val Ser Ser
        115

<210> SEQ ID NO 44
<211> LENGTH: 300
<212> TYPE: DNA
<213> ORGANISM: Homo sapiens

<400> SEQUENCE: 44
acccagtctc caggcaccct gtctttgtct ccaggggaaa gagccaccct ctcctgcagg    60
gccagtcaga gtgttagcaa ctacttagcc tggtaccagc agaaacctgg ccaggctccc    120
aggctcctca tctatggtgc atccagcagg gccactggca tcccagacag gttcagtggc    180
agtgggtctg ggacagactt cactctcacc atcagcagac tggagcctga agattttgca    240
gtgtatcact gtcagcaata ttatagtact ccgtggacgt tcggccaagg gaccaaagtg    300

<210> SEQ ID NO 45
<211> LENGTH: 100

<212> TYPE: PRT
<213> ORGANISM: Homo sapiens

<400> SEQUENCE: 45

```
Thr Gln Ser Pro Gly Thr Leu Ser Leu Ser Pro Gly Glu Arg Ala Thr
1               5                   10                  15

Leu Ser Cys Arg Ala Ser Gln Ser Val Ser Asn Tyr Leu Ala Trp Tyr
            20                  25                  30

Gln Gln Lys Pro Gly Gln Ala Pro Arg Leu Leu Ile Tyr Gly Ala Ser
        35                  40                  45

Ser Arg Ala Thr Gly Ile Pro Asp Arg Phe Ser Gly Ser Gly Ser Gly
    50                  55                  60

Thr Asp Phe Thr Leu Thr Ile Ser Arg Leu Glu Pro Glu Asp Phe Ala
65                  70                  75                  80

Val Tyr His Cys Gln Gln Tyr Tyr Ser Thr Pro Trp Thr Phe Gly Gln
                85                  90                  95

Gly Thr Lys Val
            100
```

<210> SEQ ID NO 46
<211> LENGTH: 345
<212> TYPE: DNA
<213> ORGANISM: Homo sapiens

<400> SEQUENCE: 46

```
tctggcccag gactggtgaa gccttcggag accctgtccc tcacctgcgc tgtctctggt      60
tactccatca gcagtggtta ctactggggc tggatccggc agccccccagg gaagggggctg    120
gagtggattg ggagtagcaa tcatagtggg agcacctact acaacccgtc cctcaggagt     180
cgagtcacca tatcagtaga cacgtccaag aaccaattct ccctgaaggt gaactctgtg     240
accgccgcag acacggccgt ttattactgt gcgagagagg cggggtatag cagcagctgg     300
tactttgact actggggtca gggaaccctg gtcaccgtct cctca                    345
```

<210> SEQ ID NO 47
<211> LENGTH: 115
<212> TYPE: PRT
<213> ORGANISM: Homo sapiens

<400> SEQUENCE: 47

```
Ser Gly Pro Gly Leu Val Lys Pro Ser Glu Thr Leu Ser Leu Thr Cys
1               5                   10                  15

Ala Val Ser Gly Tyr Ser Ile Ser Ser Gly Tyr Tyr Trp Gly Trp Ile
            20                  25                  30

Arg Gln Pro Pro Gly Lys Gly Leu Glu Trp Ile Gly Ser Ser Asn His
        35                  40                  45

Ser Gly Ser Thr Tyr Tyr Asn Pro Ser Leu Arg Ser Arg Val Thr Ile
    50                  55                  60

Ser Val Asp Thr Ser Lys Asn Gln Phe Ser Leu Lys Val Asn Ser Val
65                  70                  75                  80

Thr Ala Ala Asp Thr Ala Val Tyr Tyr Cys Ala Arg Glu Ala Gly Tyr
                85                  90                  95

Ser Ser Ser Trp Tyr Phe Asp Tyr Trp Gly Gln Gly Thr Leu Val Thr
                100                 105                 110

Val Ser Ser
        115
```

<210> SEQ ID NO 48

```
<211> LENGTH: 309
<212> TYPE: DNA
<213> ORGANISM: Homo sapiens

<400> SEQUENCE: 48
acgcagccgc cctcagtgtc tgcggcccca ggacagaagg tcaccatctc ctgctctgga      60
agcagctcca acattgggaa taattatgta tcctggtacc agcagctccc aggaacagcc     120
cccaaactcc tcatttatga caataataag cgaccctcag ggattcctga ccgattctct     180
ggctccaagt ctggcacgtc agccaccctg gcatcaccg actccagac tggggacgag       240 gccgattatt actgcggaac atgggatagc agcctgagtg cttgggtgtt cggcggaggg     300
acccagctg                                                              309

<210> SEQ ID NO 49
<211> LENGTH: 103
<212> TYPE: PRT
<213> ORGANISM: Homo sapiens

<400> SEQUENCE: 49

Thr Gln Pro Pro Ser Val Ser Ala Ala Pro Gly Gln Lys Val Thr Ile
1               5                   10                  15

Ser Cys Ser Gly Ser Ser Ser Asn Ile Gly Asn Asn Tyr Val Ser Trp
            20                  25                  30

Tyr Gln Gln Leu Pro Gly Thr Ala Pro Lys Leu Leu Ile Tyr Asp Asn
        35                  40                  45

Asn Lys Arg Pro Ser Gly Ile Pro Asp Arg Phe Ser Gly Ser Lys Ser
    50                  55                  60

Gly Thr Ser Ala Thr Leu Gly Ile Thr Gly Leu Gln Thr Gly Asp Glu
65                  70                  75                  80

Ala Asp Tyr Tyr Cys Gly Thr Trp Asp Ser Ser Leu Ser Ala Trp Val
                85                  90                  95

Phe Gly Gly Gly Thr Gln Leu
            100

<210> SEQ ID NO 50
<211> LENGTH: 6
<212> TYPE: PRT
<213> ORGANISM: Homo sapiens
<220> FEATURE:
<221> NAME/KEY: A1
<222> LOCATION: (2)..(2)
<223> OTHER INFORMATION: Xaa is any amino acid selected from valine and
      leucine
<220> FEATURE:
<221> NAME/KEY: A2
<222> LOCATION: (6)..(6)
<223> OTHER INFORMATION: Xaa is any amino acid selected from glutamic
      acide and glutamine

<400> SEQUENCE: 50

Gln Xaa Gln Leu Gln Xaa
1               5

<210> SEQ ID NO 51
<211> LENGTH: 4
<212> TYPE: PRT
<213> ORGANISM: Homo sapiens

<400> SEQUENCE: 51

Gln Ser Val Leu
1
```

```
<210> SEQ ID NO 52
<211> LENGTH: 4
<212> TYPE: PRT
<213> ORGANISM: Homo sapiens
<220> FEATURE:
<221> NAME/KEY: A1
<222> LOCATION: (4)..(4)
<223> OTHER INFORMATION: Xaa is any amino acid selected from leucine and
      methionine

<400> SEQUENCE: 52

Glu Ile Val Xaa
1

<210> SEQ ID NO 53
<211> LENGTH: 3
<212> TYPE: PRT
<213> ORGANISM: Homo sapiens

<400> SEQUENCE: 53

Thr Val Leu
1

<210> SEQ ID NO 54
<211> LENGTH: 3
<212> TYPE: PRT
<213> ORGANISM: Homo sapiens
<220> FEATURE:
<221> NAME/KEY: A1
<222> LOCATION: (1)..(1)
<223> OTHER INFORMATION: Xaa is any amino acid selected from aspartic
      acid and glutamic acid

<400> SEQUENCE: 54

Xaa Ile Lys
1

<210> SEQ ID NO 55
<211> LENGTH: 462
<212> TYPE: PRT
<213> ORGANISM: Homo sapiens

<400> SEQUENCE: 55

Met Asp Trp Thr Trp Arg Ile Leu Phe Leu Val Ala Ala Thr Gly
1               5                   10                  15

Ala His Ser Gln Met Gln Leu Leu Glu Ser Gly Pro Gly Leu Val Lys
                20                  25                  30

Pro Ser Glu Thr Leu Ser Leu Thr Cys Thr Val Ser Gly Gly Ser Ile
            35                  40                  45

Trp Gly Trp Ile Arg Gln Pro Pro Gly Lys Gly Leu Glu Trp Ile Gly
    50                  55                  60

Ser Ile Tyr Ser Ser Gly Ser Thr Tyr Tyr Asn Pro Ser Leu Lys Ser
65                  70                  75                  80

Arg Val Thr Thr Ser Val Asp Thr Ser Lys Asn Gln Phe Ser Leu Arg
                85                  90                  95

Leu Ser Ser Val Thr Ala Ala Asp Thr Ala Val Tyr Tyr Cys Val Ala
            100                 105                 110

Trp Phe Gly Asp Leu Leu Ser Leu Lys Gly Val Glu Leu Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160
```

-continued

```
Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
        180                 185                 190

Leu Gln Ser Ser Gly Leu Tyr Ser Leu Ser Ser Val Thr Val Pro
    195                 200                 205

Ser Ser Asn Phe Gly Thr Gln Thr Tyr Thr Cys Asn Val Asp His Lys
210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 56
<211> LENGTH: 235
<212> TYPE: PRT
<213> ORGANISM: Homo sapiens

<400> SEQUENCE: 56

Met Ala Trp Ala Leu Leu Leu Thr Leu Leu Thr Gln Gly Thr Gly
1               5                   10                  15

Ser Trp Ala Gln Ser Glu Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Tyr Val Tyr Trp Tyr Gln Gln Leu Pro Gly Thr Ala Pro
    50                  55                  60

Lys Leu Leu Ile Tyr Arg Asn Asn Gln Arg Pro Ser Gly Val Pro Asp
65                  70                  75                  80
```

```
Arg Phe Ser Gly Ser Lys Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Asp Ser Leu Ser Ala Trp Val Phe Gly Gly Gly Thr Gln Leu Asp Ile
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 57
<211> LENGTH: 462
<212> TYPE: PRT
<213> ORGANISM: Homo sapiens

<400> SEQUENCE: 57

Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Trp Gly Trp Ile Arg Gln Pro Pro Gly Lys Gly Leu Glu Trp Ile Gly
    50                  55                  60

Ser Ile Tyr Ser Ser Gly Ser Thr Tyr Tyr Asn Pro Ser Leu Lys Ser
65                  70                  75                  80

Arg Val Thr Thr Ser Val Asp Thr Ser Lys Asn Gln Phe Ser Leu Arg
                85                  90                  95

Leu Ser Ser Val Thr Ala Ala Asp Thr Ala Val Tyr Tyr Cys Val Ala
            100                 105                 110

Trp Phe Gly Asp Leu Leu Ser Leu Lys Gly Val Glu Leu Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220
```

-continued

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Gln Phe Asn Trp Tyr Val Asp Gly Val Glu Val His Asn Ala Lys Thr
290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 58
<211> LENGTH: 235
<212> TYPE: PRT
<213> ORGANISM: Homo sapiens

<400> SEQUENCE: 58

Met Ala Gly Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Tyr Val Tyr Trp Tyr Gln Gln Leu Pro Gly Thr Ala Pro
    50                  55                  60

Lys Leu Leu Ile Tyr Arg Asn Asn Gln Arg Pro Ser Gly Val Pro Asp
65                  70                  75                  80

Arg Phe Ser Gly Ser Lys Ser Gly Thr Ser Ala Ser Leu Ala Ile Ser
            85                  90                  95

Gly Leu Arg Ser Glu Asp Glu Ala Asp Tyr Tyr Cys Ala Ala Trp Asp
        100                 105                 110

Asp Ser Leu Ser Ala Trp Val Phe Gly Gly Gly Thr Gln Leu Thr Val
    115                 120                 125

Leu Gly Gln Pro Lys Ala Ala Pro Ser Val Thr Leu Phe Pro Pro Ser
    130                 135                 140

```
Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
            165                 170                 175

Pro Val Lys Ala Gly Val Glu Thr Thr Thr Pro Ser Lys Gln Ser Asn
        180                 185                 190

Asn Lys Tyr Ala Ala Ser Ser Tyr Leu Ser Leu Thr Pro Glu Gln Trp
    195                 200                 205

Lys Ser His Arg Ser Tyr Ser Cys Gln Val Thr His Glu Gly Ser Thr
210                 215                 220

Val Glu Lys Thr Val Ala Pro Thr Glu Cys Ser
225                 230                 235

<210> SEQ ID NO 59
<211> LENGTH: 796
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t

<400> SEQUENCE: 59
nggcccaggc ggccgagctc gtgctgactc agccaccttc agcgtctggg acccccgggc      60
agagggtcac catctcttgt tctggaagca gctccaacat cggaagtaat tatgtatact    120
ggtaccagca gctcccagga acggccccca aactcctcat ctataggaat aatcagcggc    180 cctcagggt ccctgaccga ttctctggct ccaagtctgg cacctcagcc tccctggcca    240
tcagtgggct ccggtccgag gatgaggctg attattactg tgcagcatgg gatgacagcc    300
tgagtgcttg ggtgttcggc ggaggcaccc agctgaccgt cctcggtggt ggttcctcta    360
gatcttcctc ctctggtggc ggtggctcgg gcggtggtgg ggaggtgcag ctggtgcagt    420
ctggcccagg actggtgaag ccttcggaga ccctgtccct cacctgcact gtctctggtg    480
gctccatctg ggctggatc cgccagcccc cagggaaggg gctggagtgg attgggagta    540
tctattctag tgggagcacc tactacaacc cgtccctcaa gagtcgagtc accacatccg    600
tagacacgtc caagaaccag ttctccctga ggctgagctc tgtgaccgcc gcagacacgg    660
ctgtgtatta ctgtgtggcg tggttcgggg acttattatc gttgaagggg gttgaattgt    720
ggggccaggg aaccctggtc accgtctcct cagcttccac caagggccca tcggtcacta    780
gtggccaggc cggccn                                                    796

<210> SEQ ID NO 60
<211> LENGTH: 261
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 60

Xaa Ala Glu Leu Val Leu Thr Gln Pro Pro Ser Ala Ser Gly Thr Pro
1               5                   10                  15

Gly Gln Arg Val Thr Ile Ser Cys Ser Gly Ser Ser Asn Ile Gly
            20                  25                  30
```

```
Ser Asn Tyr Val Tyr Trp Tyr Gln Gln Leu Pro Gly Thr Ala Pro Lys
            35                  40                  45

Leu Leu Ile Tyr Arg Asn Asn Gln Arg Pro Ser Gly Val Pro Asp Arg
 50                  55                  60

Phe Ser Gly Ser Lys Ser Gly Thr Ser Ala Ser Leu Ala Ile Ser Gly
 65                  70                  75                  80

Leu Arg Ser Glu Asp Glu Ala Asp Tyr Tyr Cys Ala Ala Trp Asp Asp
                 85                  90                  95

Ser Leu Ser Ala Trp Val Phe Gly Gly Gly Thr Gln Leu Thr Val Leu
            100                 105                 110

Gly Gly Gly Ser Arg Ser Ser Ser Gly Gly Gly Ser Gly
            115                 120                 125

Gly Gly Gly Glu Val Gln Leu Val Gln Ser Gly Pro Gly Leu Val Lys
            130                 135                 140

Pro Ser Glu Thr Leu Ser Leu Thr Cys Thr Val Ser Gly Gly Ser Ile
145                 150                 155                 160

Trp Gly Trp Ile Arg Gln Pro Pro Gly Lys Gly Leu Glu Trp Ile Gly
                165                 170                 175

Ser Ile Tyr Ser Ser Gly Ser Thr Tyr Tyr Asn Pro Ser Leu Lys Ser
            180                 185                 190

Arg Val Thr Thr Ser Val Asp Thr Ser Lys Asn Gln Phe Ser Leu Arg
            195                 200                 205

Leu Ser Ser Val Thr Ala Ala Asp Thr Ala Val Tyr Tyr Cys Val Ala
210                 215                 220

Trp Phe Gly Asp Leu Leu Ser Leu Lys Gly Val Glu Leu Trp Gly Gln
225                 230                 235                 240

Gly Thr Leu Val Thr Val Ser Ser Ala Ser Thr Lys Gly Pro Ser Val
                245                 250                 255

Thr Ser Gly Gln Ala
            260
```

<210> SEQ ID NO 61
<211> LENGTH: 796
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t

<400> SEQUENCE: 61

```
nggcccaggc ggccgagctc gtgctgactc agccaccctc agtgtctggg acccccgggc      60
agagggtcac cgtctcttgt tctggaagca gctctaacat cggaagtaaa aatgtatact     120
ggtaccagca gctcccagga acggccccca aactcctcat ctataggaat aatcagcggc     180
cctcaggggt ccctgaccga ttctctggct ccaagtctgg cacctcagcc tccctggcca     240
tcagtgggct ccggtccgag gatgaggctg attattactg tgcagcatgg gatgacagcc     300
tgagtggttg ggtgttcagc ggaggcacca aggtgaccgt cctaggtggt ggttcctcta     360
gatcttcctc ctctggtggc ggtggctcgg cggtggtgg ggaggtgcag ctggtggagt     420
ctggcccagg actggtgaag ccttcggaga ccctgtccct cacctgcact gtctctggtg     480
gctccatctg ggctggatc cgccagcccc cagggaaggg gctggagtgg attgggagta     540
tctattctag tgggagcacc tactacaacc cgtccctcaa gagtcgagtc accatatccg     600
```

```
tagacacgtc caagaaccag ttctccctga ggctgagctc tgtgaccgcc gcagacacgg    660
ctgtgtatta ctgtgtggtg tggttcgggg acttattatc gttgaagggg gtcgaattgt    720
ggggccaggg aaccctggtc accgtctcct cagcttccac caagggccca tcggtcacta    780
gtggccaggc cggccn                                                    796
```

<210> SEQ ID NO 62
<211> LENGTH: 261
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 62

```
Xaa Ala Glu Leu Val Leu Thr Gln Pro Pro Ser Val Ser Gly Thr Pro
1               5                   10                  15

Gly Gln Arg Val Thr Val Ser Cys Ser Gly Ser Ser Ser Asn Ile Gly
                20                  25                  30

Ser Lys Asn Val Tyr Trp Tyr Gln Gln Leu Pro Gly Thr Ala Pro Lys
            35                  40                  45

Leu Leu Ile Tyr Arg Asn Asn Gln Arg Pro Ser Gly Val Pro Asp Arg
        50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Ala Ala Trp Asp Asp
                85                  90                  95

Ser Leu Ser Gly Trp Val Phe Ser Gly Gly Thr Lys Val Thr Val Leu
            100                 105                 110

Gly Gly Gly Ser Ser Arg Ser Ser Ser Gly Gly Gly Gly Ser Gly
        115                 120                 125

Gly Gly Gly Glu Val Gln Leu Val Glu Ser Gly Pro Gly Leu Val Lys
    130                 135                 140

Pro Ser Glu Thr Leu Ser Leu Thr Cys Thr Val Ser Gly Gly Ser Ile
145                 150                 155                 160

Trp Gly Trp Ile Arg Gln Pro Pro Gly Lys Gly Leu Glu Trp Ile Gly
                165                 170                 175

Ser Ile Tyr Ser Ser Gly Ser Thr Tyr Tyr Asn Pro Ser Leu Lys Ser
            180                 185                 190

Arg Val Thr Ile Ser Val Asp Thr Ser Lys Asn Gln Phe Ser Leu Arg
        195                 200                 205

Leu Ser Ser Val Thr Ala Ala Asp Thr Ala Val Tyr Tyr Cys Val Val
    210                 215                 220

Trp Phe Gly Asp Leu Leu Ser Leu Lys Gly Val Glu Leu Trp Gly Gln
225                 230                 235                 240

Gly Thr Leu Val Thr Val Ser Ser Ala Ser Thr Lys Gly Pro Ser Val
                245                 250                 255

Thr Ser Gly Gln Ala
            260
```

<210> SEQ ID NO 63
<211> LENGTH: 796
<212> TYPE: DNA
<213> ORGANISM: Homo sapiens
<220> FEATURE:
<221> NAME/KEY: misc_feature
<222> LOCATION: (1)..(1)

<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t

<400> SEQUENCE: 63

```
nggcccaggc ggccgggctc gtggtgacgc agccgccctc agtgtctggg accccggggc    60
agagggtcac catctcttgt tctggaagca gctccaacat cggaagtagt tatgtatact   120
ggtaccagca gctcccagga acggccccca aactcctcat ctataggaat aatcagcggc   180
cctcaggggt ccctgaccga ttctctggct ccaagtctgg cacctcagcc tccctggcca   240
tcagtgggct ccggtccgag gatgaggctg attattactg tgcagcatgg gatgacagcc   300
tgagtggttg ggtgttcggc ggaggcaccg agctgaccgt cctcggtggt ggttcctcta   360
gatcttcctc ctctggtggc ggtggctcgg gcggtggtgg ggaggtgcag ctggtggagt   420
ctggcccagg actggtgaag ccttcggaga ccctgtccca cacctgcact gtctctggtg   480
gctccatctg gggctggatc cgccagcccc cagggaaggg gctggagtgg attgggagta   540
tctattctag tgggagcacc tactacaacc cgtccctcaa gagtcgagtc accatatccg   600
tagacacgtc caagaaccag ttctccctga ggctgagctc tgtgaccgcc gcagacacgg   660
ctgtgtatta ctgtgtggtg tggttcgggg acttattatc gttgaagggg gttgaattgt   720
ggggccaggg aaccctggtc accgtctcct cagcttccac caagggccca tcggtcacta   780
gtggccaggc cggccn                                                   796
```

<210> SEQ ID NO 64
<211> LENGTH: 261
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 64

```
Xaa Ala Gly Leu Val Val Thr Gln Pro Pro Ser Val Ser Gly Thr Pro
1               5                   10                  15

Gly Gln Arg Val Thr Ile Ser Cys Ser Gly Ser Ser Asn Ile Gly
            20                  25                  30

Ser Ser Tyr Val Tyr Trp Tyr Gln Gln Leu Pro Gly Thr Ala Pro Lys
        35                  40                  45

Leu Leu Ile Tyr Arg Asn Asn Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Ala Ala Trp Asp Asp
                85                  90                  95

Ser Leu Ser Gly Trp Val Phe Gly Gly Gly Thr Glu Leu Thr Val Leu
            100                 105                 110

Gly Gly Gly Ser Ser Arg Ser Ser Ser Gly Gly Gly Gly Ser Gly
        115                 120                 125

Gly Gly Gly Glu Val Gln Leu Val Glu Ser Gly Pro Gly Leu Val Lys
    130                 135                 140

Pro Ser Glu Thr Leu Ser His Thr Cys Thr Val Ser Gly Gly Ser Ile
145                 150                 155                 160

Trp Gly Trp Ile Arg Gln Pro Pro Gly Lys Gly Leu Glu Trp Ile Gly
                165                 170                 175
```

```
Ser Ile Tyr Ser Ser Gly Ser Thr Tyr Tyr Asn Pro Ser Leu Lys Ser
            180                 185                 190

Arg Val Thr Ile Ser Val Asp Thr Ser Lys Asn Gln Phe Ser Leu Arg
        195                 200                 205

Leu Ser Ser Val Thr Ala Ala Asp Thr Ala Val Tyr Tyr Cys Val Val
    210                 215                 220

Trp Phe Gly Asp Leu Leu Ser Leu Lys Gly Val Glu Leu Trp Gly Gln
225                 230                 235                 240

Gly Thr Leu Val Thr Val Ser Ser Ala Ser Thr Lys Gly Pro Ser Val
                245                 250                 255

Thr Ser Gly Gln Ala
            260

<210> SEQ ID NO 65
<211> LENGTH: 796
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t

<400> SEQUENCE: 65
nggcccaggc ggccgagcac gtggtgaccc aggagccctc agtgtctggg acccccgggc    60
agagggtcac catctcttgt tctggaagca gctccaacat cggaagtaat tatgtatact   120
ggtaccagca gctcccagga acggccccca aactcctcat ctataggaat aatcagcggc   180 cctcagggc  ccctgaccga ttctctggct ccaagtctgg cacctcagcc tccctggcca   240
tcagtgggct ccggtccgag gatgaggctg attattactg tgcagcatgg gatgacagcc   300
tgagtggttg ggtgttcggc ggagggacca agctgaccgt cctaggcggt ggttcctcta   360
gatcttcctc ctctggtggc ggtggctcgg gcggtggtgg gcaggtgcag ctgcaggagt   420
cgggcccagg actggtgaag ccttcggaga ccctgtccct cacctgcact gtctctggtg   480
gctccatctg gggctggatc cgccagcccc cagggaaggg gctggagtgg attgggagta   540
tctattctag tgggagcacc tactacaacc cgtccctcaa gagtcgagtc accatatccg   600
tagacacgtc caagaaccag ttctccctga ggctgagctc tgtgaccgcc gcagacacgg   660
ctgtgtatta ctgtgtggtg tggttcgggg acttattatc gttgaagggg gttgaattgt   720
ggggccaggg aaccctggtc accgtctcct cagcttccac caagggccca tcggtcacta   780
gtggccaggc cggccn                                                   796

<210> SEQ ID NO 66
<211> LENGTH: 261
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 66

Xaa Ala Glu His Val Val Thr Gln Glu Pro Ser Val Ser Gly Thr Pro
1               5                   10                  15

Gly Gln Arg Val Thr Ile Ser Cys Ser Gly Ser Ser Asn Ile Gly
            20                  25                  30
```

```
Ser Asn Tyr Val Tyr Trp Tyr Gln Gln Leu Pro Gly Thr Ala Pro Lys
         35                  40                  45

Leu Leu Ile Tyr Arg Asn Asn Gln Arg Pro Ser Gly Ala Pro Asp Arg
 50                  55                  60

Phe Ser Gly Ser Lys Ser Gly Thr Ser Ala Ser Leu Ala Ile Ser Gly
 65                  70                  75                  80

Leu Arg Ser Glu Asp Glu Ala Asp Tyr Tyr Cys Ala Ala Trp Asp Asp
                 85                  90                  95

Ser Leu Ser Gly Trp Val Phe Gly Gly Gly Thr Lys Leu Thr Val Leu
            100                 105                 110

Gly Gly Gly Ser Ser Arg Ser Ser Ser Gly Gly Gly Ser Gly
            115                 120                 125

Gly Gly Gly Gln Val Gln Leu Gln Glu Ser Gly Pro Gly Leu Val Lys
    130                 135                 140

Pro Ser Glu Thr Leu Ser Leu Thr Cys Thr Val Ser Gly Gly Ser Ile
145                 150                 155                 160

Trp Gly Trp Ile Arg Gln Pro Pro Gly Lys Gly Leu Glu Trp Ile Gly
                165                 170                 175

Ser Ile Tyr Ser Ser Gly Ser Thr Tyr Tyr Asn Pro Ser Leu Lys Ser
            180                 185                 190

Arg Val Thr Ile Ser Val Asp Thr Ser Lys Asn Gln Phe Ser Leu Arg
        195                 200                 205

Leu Ser Ser Val Thr Ala Ala Asp Thr Ala Val Tyr Tyr Cys Val Val
    210                 215                 220

Trp Phe Gly Asp Leu Leu Ser Leu Lys Gly Val Glu Leu Trp Gly Gln
225                 230                 235                 240

Gly Thr Leu Val Thr Val Ser Ser Ala Ser Thr Lys Gly Pro Ser Val
                245                 250                 255

Thr Ser Gly Gln Ala
            260

<210> SEQ ID NO 67
<211> LENGTH: 796
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t

<400> SEQUENCE: 67
nggcccaggc ggccgagctc gtgctgactc agccaccac  agtgtctggg accccgggc       60 agagggtcac catctcttgt tctggaagca gctccaacat cggaagtaaa aatgtatact     120
ggtaccagca gctcccagga acggccccca aactcctcat ctataggaat aatcagcggc     180
cctcaggggt ccctgaccga ttctctggct ccaagtctgg cacctcagcc tccctggcca     240
tcagtgggct ccggtccgag gatgaggctg attattactg tgcagcatgg gatgacagcc     300
tgagtggttg ggtgttcggc ggaggcacca aggtgaccgt cctaggtggt ggttcctcta     360
gatcttcctc ctctggtggc ggtggctcgg cggtggtgg gcagatcacc ttgaaggagt     420
ctggcccagg actggtgaag ccttcggaga ccctgtccct cacctgcact gtctctggtg     480
gttccatctg gggctggatc cgccagcccc cagggaaggg gctggagtgg attgggagta     540
```

-continued

```
tctattctag tgggagcacc tactacaacc cgtccctcaa gagtcgagtc accatatccg    600
tagacacgtc cgagaaccag ttctccctga ggctgagctc tgtgaccgcc gcagacacgg    660
ctgtgtatta ctgtgtggtg tggttcgggg acttattatc gttgaagggg gttgaattgt    720
ggggccaggg aaccctggtc accgtctcct cagcttccac caagggccca tcggtcacta    780
gtggccaggc cggccn                                                    796
```

<210> SEQ ID NO 68
<211> LENGTH: 261
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 68

```
Xaa Ala Glu Leu Val Leu Thr Gln Pro Pro Thr Val Ser Gly Thr Pro
1               5                   10                  15

Gly Gln Arg Val Thr Ile Ser Cys Ser Gly Ser Ser Ser Asn Ile Gly
            20                  25                  30

Ser Lys Asn Val Tyr Trp Tyr Gln Gln Leu Pro Gly Thr Ala Pro Lys
        35                  40                  45

Leu Leu Ile Tyr Arg Asn Asn Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Ala Ala Trp Asp Asp
                85                  90                  95

Ser Leu Ser Gly Trp Val Phe Gly Gly Gly Thr Lys Val Thr Val Leu
            100                 105                 110

Gly Gly Gly Ser Ser Arg Ser Ser Ser Gly Gly Gly Gly Ser Gly
        115                 120                 125

Gly Gly Gly Gln Ile Thr Leu Lys Glu Ser Gly Pro Gly Leu Val Lys
    130                 135                 140

Pro Ser Glu Thr Leu Ser Leu Thr Cys Thr Val Ser Gly Gly Ser Ile
145                 150                 155                 160

Trp Gly Trp Ile Arg Gln Pro Pro Gly Lys Gly Leu Glu Trp Ile Gly
                165                 170                 175

Ser Ile Tyr Ser Ser Gly Ser Thr Tyr Tyr Asn Pro Ser Leu Lys Ser
            180                 185                 190

Arg Val Thr Ile Ser Val Asp Thr Ser Glu Asn Gln Phe Ser Leu Arg
        195                 200                 205

Leu Ser Ser Val Thr Ala Ala Asp Thr Ala Val Tyr Tyr Cys Val Val
    210                 215                 220

Trp Phe Gly Asp Leu Leu Ser Leu Lys Gly Val Glu Leu Trp Gly Gln
225                 230                 235                 240

Gly Thr Leu Val Thr Val Ser Ser Ala Ser Thr Lys Gly Pro Ser Val
                245                 250                 255

Thr Ser Gly Gln Ala
            260
```

<210> SEQ ID NO 69
<211> LENGTH: 796
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t

<400> SEQUENCE: 69
nggcccaggc ggccgagctc cacatgaccc agtctccagg caccctgtct ttgtctccag    60
gggaaagagc caccctctcc tgcagggcca gtcagagtgt tagcaactac ttagcctggt   120
accagcagaa acctggccag gctcccaggc tcctcatcta tggtgcatcc agcagggcca   180
ctggcatccc agacaggttc agtggcagtg ggtctgggac agacttcact ctcaccatca   240
gcagactgga gcctgaagat tttgcagtgt atcactgtca gcaatattat agtactccgt   300
ggacgttcgg ccaagggacc aaagtggata tcaaaggtgg ttcctctaga tcttcctcct   360
ctggtggcgg tggctcgggc ggtggtgggt caggtgcagct gcaggagtcg ggcccaggac   420
tggtgaagcc ttcggagacc ctgtccctca cctgcactgt ctctggtggc tccatcagca   480
gtactagtta ctactggggc tggatccgcc agcccccagg gaaggggctg gagtggattg   540
ggagtatctc ttatagtggg agcacctact acaacccgtc cctcaagagt cgagtcacca   600
tatccgtaga cacgtccaag aaccagttct ccctgaagct gacctctgtg accgccgcag   660
acacggctgt gtattactgt gcgaggatac tatggttcgg agagtaccta ggggactact   720
ggggccaggg aaccctggtc accgtctcct cagcctccac caagggccca tcggtcacta   780
gtggccaggc cggccn                                                   796

<210> SEQ ID NO 70
<211> LENGTH: 261
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 70

Xaa Ala Glu Leu His Met Thr Gln Ser Pro Gly Thr Leu Ser Leu Ser
1               5                   10                  15

Pro Gly Glu Arg Ala Thr Leu Ser Cys Arg Ala Ser Gln Ser Val Ser
            20                  25                  30

Asn Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr His Cys Gln Gln Tyr Tyr Ser Thr
                85                  90                  95

Pro Trp Thr Phe Gly Gln Gly Thr Lys Val Asp Ile Lys Gly Gly Ser
            100                 105                 110

Ser Arg Ser Ser Ser Ser Gly Gly Gly Gly Ser Gly Gly Gly Gly Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Gly Ser Ile Ser Ser Thr Ser
145                 150                 155                 160

Tyr Tyr Trp Gly Trp Ile Arg Gln Pro Pro Gly Lys Gly Leu Glu Trp

```
                     165                 170                 175
Ile Gly Ser Ile Ser Tyr Ser Gly Ser Thr Tyr Asn Pro Ser Leu
            180                 185                 190

Lys Ser Arg Val Thr Ile Ser Val Asp Thr Ser Lys Asn Gln Phe Ser
        195                 200                 205

Leu Lys Leu Thr Ser Val Thr Ala Ala Asp Thr Ala Val Tyr Tyr Cys
    210                 215                 220

Ala Arg Ile Leu Trp Phe Gly Glu Tyr Leu Gly Asp Tyr Trp Gly Gln
225                 230                 235                 240

Gly Thr Leu Val Thr Val Ser Ser Ala Ser Thr Lys Gly Pro Ser Val
                245                 250                 255

Thr Ser Gly Gln Ala
            260
```

<210> SEQ ID NO 71
<211> LENGTH: 808
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t

<400> SEQUENCE: 71

```
nggcccaggc ggccgagctc ctggtgacgc agccgccctc agtgtctgcg gccccaggac      60
agaaggtcac catctcctgc tctggaagca gctccaacat tgggaataat tatgtatcct     120
ggtaccagca gctcccagga acagccccca aactcctcat ttatgacaat aataagcgac     180
cctcagggat tcctgaccga ttctctggct ccaagtctgg cacgtcagcc accctgggca     240
tcaccggact ccagactggg gacgaggccg attattactg cggaacatgg gatagcagcc     300
tgagtgcttg ggtgttcggc ggagggaccc agctgaccgt cctcggcggt ggttcctcta     360
gatcttcctc ctctggtggc ggtggctcgg cggtggtgg agaggtgcag ctggtgcagt     420
ctggcccagg actggtgaag ccttcggaga ccctgtccct cacctgcgct gtctctggtt     480
actccatcag cagtggttac tactgggct ggatccggca gccccaggg aaggggctgg       540
agtggattgg agtagcaat catagtggga gcacctacta caacccgtcc ctcaggagtc      600
gagtcaccat atcagtagac acgtccaaga accaattctc cctgaaggtg aactctgtga     660
ccgccgcaga cacggccgtt tattactgtg cgagagaggc ggggtatagc agcagctggt     720
actttgacta ctggggtcag ggaaccctgg tcaccgtctc ctcagcctcc accaagggcc     780
catcggtcac tagtggccag gccggccn                                        808
```

<210> SEQ ID NO 72
<211> LENGTH: 265
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 72

```
Xaa Ala Glu Leu Leu Val Thr Gln Pro Pro Ser Val Ser Ala Ala Pro
1               5                   10                  15

Gly Gln Lys Val Thr Ile Ser Cys Ser Gly Ser Ser Ser Asn Ile Gly
```

```
                20                  25                  30
Asn Asn Tyr Val Ser Trp Tyr Gln Gln Leu Pro Gly Thr Ala Pro Lys
            35                  40                  45

Leu Leu Ile Tyr Asp Asn Asn Lys Arg Pro Ser Gly Ile Pro Asp Arg
 50                  55                  60

Phe Ser Gly Ser Lys Ser Gly Thr Ser Ala Thr Leu Gly Ile Thr Gly
 65                  70                  75                  80

Leu Gln Thr Gly Asp Glu Ala Asp Tyr Tyr Cys Gly Thr Trp Asp Ser
                85                  90                  95

Ser Leu Ser Ala Trp Val Phe Gly Gly Gly Thr Gln Leu Thr Val Leu
            100                 105                 110

Gly Gly Gly Ser Ser Arg Ser Ser Ser Gly Gly Gly Gly Ser Gly
        115                 120                 125

Gly Gly Gly Glu Val Gln Leu Val Gln Ser Gly Pro Gly Leu Val Lys
        130                 135                 140

Pro Ser Glu Thr Leu Ser Leu Thr Cys Ala Val Ser Gly Tyr Ser Ile
145                 150                 155                 160

Ser Ser Gly Tyr Tyr Trp Gly Trp Ile Arg Gln Pro Pro Gly Lys Gly
                165                 170                 175

Leu Glu Trp Ile Gly Ser Ser Asn His Ser Gly Ser Thr Tyr Tyr Asn
            180                 185                 190

Pro Ser Leu Arg Ser Arg Val Thr Ile Ser Val Asp Thr Ser Lys Asn
        195                 200                 205

Gln Phe Ser Leu Lys Val Asn Ser Val Thr Ala Ala Asp Thr Ala Val
    210                 215                 220

Tyr Tyr Cys Ala Arg Glu Ala Gly Tyr Ser Ser Ser Trp Tyr Phe Asp
225                 230                 235                 240

Tyr Trp Gly Gln Gly Thr Leu Val Thr Val Ser Ser Ala Ser Thr Lys
                245                 250                 255

Gly Pro Ser Val Thr Ser Gly Gln Ala
            260                 265

<210> SEQ ID NO 73
<211> LENGTH: 443
<212> TYPE: PRT
<213> ORGANISM: Homo sapiens

<400> SEQUENCE: 73

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Trp Gly Trp
            20                  25                  30

Ile Arg Gln Pro Pro Gly Lys Gly Leu Glu Trp Ile Gly Ser Ile Tyr
        35                  40                  45

Ser Ser Gly Ser Thr Tyr Tyr Asn Pro Ser Leu Lys Ser Arg Val Thr
 50                  55                  60

Thr Ser Val Asp Thr Ser Lys Asn Gln Phe Ser Leu Arg Leu Ser Ser
 65                  70                  75                  80

Val Thr Ala Ala Asp Thr Ala Val Tyr Tyr Cys Val Ala Trp Phe Gly
                85                  90                  95

Asp Leu Leu Ser Leu Lys Gly Val Glu Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
```

```
                130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
                180                 185                 190

Phe Gly Thr Gln Thr Tyr Thr Cys Asn Val Asp His Lys Pro Ser Asn
                195                 200                 205

Thr Lys Val Asp Lys Thr Val Glu Arg Lys Cys Cys Val Glu Cys Pro
                210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
                290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 74
<211> LENGTH: 216
<212> TYPE: PRT
<213> ORGANISM: Homo sapiens

<400> SEQUENCE: 74

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
                50                  55                  60

Gly Ser Lys Ser Gly Thr Ser Ala Ser Leu Ala Ile Ser Gly Leu Arg
```

```
            65                  70                  75                  80
Ser Glu Asp Glu Ala Asp Tyr Tyr Cys Ala Ala Trp Asp Asp Ser Leu
                    85                  90                  95

Ser Ala Trp Val Phe Gly Gly Gly Thr Gln Leu Thr Val Leu Gly Gln
            100                 105                 110

Pro Lys Ala Ala Pro Ser Val Thr Leu Phe Pro Ser Ser Glu Glu
        115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 75
<211> LENGTH: 443
<212> TYPE: PRT
<213> ORGANISM: Homo sapiens

<400> SEQUENCE: 75

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Trp Gly Trp
            20                  25                  30

Ile Arg Gln Pro Pro Gly Lys Gly Leu Glu Trp Ile Gly Ser Ile Tyr
        35                  40                  45

Ser Ser Gly Ser Thr Tyr Tyr Asn Pro Ser Leu Lys Ser Arg Val Thr
    50                  55                  60

Ile Ser Val Asp Thr Ser Lys Asn Gln Phe Ser Leu Arg Leu Ser Ser
65                  70                  75                  80

Val Thr Ala Ala Asp Thr Ala Val Tyr Tyr Cys Val Val Trp Phe Gly
            85                  90                  95

Asp Leu Leu Ser Leu Lys Gly Val Glu Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
        210                 215                 220

Pro Cys Pro Ala Pro Pro Val Ala Gly Pro Ser Val Phe Leu Phe Pro
```

```
                225                 230                 235                 240
Pro Lys Pro Lys Asp Thr Leu Met Ile Ser Arg Thr Pro Glu Val Thr
                    245                 250                 255

Cys Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
            290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                    325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                    405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
            435                 440

<210> SEQ ID NO 76
<211> LENGTH: 216
<212> TYPE: PRT
<213> ORGANISM: Homo sapiens

<400> SEQUENCE: 76

Gln Ser Val Leu Thr Gln Pro Pro Ser Val Ser Gly Thr Pro Gly Gln
1               5                   10                  15

Arg Val Thr Val Ser Cys Ser Gly Ser Ser Ser Asn Ile Gly Ser Lys
                20                  25                  30

Asn Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Ser Gly Gly Thr Lys Val Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
```

```
                     165                 170                 175
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 77
<211> LENGTH: 443
<212> TYPE: PRT
<213> ORGANISM: Homo sapiens

<400> SEQUENCE: 77

Gln Leu Gln Leu Gln Glu Ser Gly Pro Gly Leu Val Lys Pro Ser Glu
1               5                   10                  15

Thr Leu Ser His Thr Cys Thr Val Ser Gly Gly Ser Ile Trp Gly Trp
            20                  25                  30

Ile Arg Gln Pro Pro Gly Lys Gly Leu Glu Trp Ile Gly Ser Ile Tyr
        35                  40                  45

Ser Ser Gly Ser Thr Tyr Tyr Asn Pro Ser Leu Lys Ser Arg Val Thr
50                  55                  60

Ile Ser Val Asp Thr Ser Lys Asn Gln Phe Ser Leu Arg Leu Ser Ser
65                  70                  75                  80

Val Thr Ala Ala Asp Thr Ala Val Tyr Tyr Cys Val Val Trp Phe Gly
                85                  90                  95

Asp Leu Leu Ser Leu Lys Gly Val Glu Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
```

```
                    325                 330                 335
Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440
```

<210> SEQ ID NO 78
<211> LENGTH: 216
<212> TYPE: PRT
<213> ORGANISM: Homo sapiens

<400> SEQUENCE: 78

```
Gln Ser Val Leu Thr Gln Pro Pro Ser Val Ser Gly Thr Pro Gly Gln
1               5                   10                  15

Arg Val Thr Ile Ser Cys Ser Gly Ser Ser Asn Ile Gly Ser Ser
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Glu Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 79
<211> LENGTH: 216
<212> TYPE: PRT
<213> ORGANISM: Homo sapiens

<400> SEQUENCE: 79

```
Gln Ser Val Leu Thr Gln Glu Pro Ser Val Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Ala Pro Asp Arg Phe Ser
50                      55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 80
<211> LENGTH: 443
<212> TYPE: PRT
<213> ORGANISM: Homo sapiens

<400> SEQUENCE: 80

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Trp Gly Trp
            20                  25                  30

Ile Arg Gln Pro Pro Gly Lys Gly Leu Glu Trp Ile Gly Ser Ile Tyr
            35                  40                  45

Ser Ser Gly Ser Thr Tyr Tyr Asn Pro Ser Leu Lys Ser Arg Val Thr
50                      55                  60

Ile Ser Val Asp Thr Ser Glu Asn Gln Phe Ser Leu Arg Leu Ser Ser
65                  70                  75                  80

Val Thr Ala Ala Asp Thr Ala Val Tyr Tyr Cys Val Val Trp Phe Gly
                85                  90                  95

Asp Leu Leu Ser Leu Lys Gly Val Glu Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 81
<211> LENGTH: 216
<212> TYPE: PRT
<213> ORGANISM: Homo sapiens

<400> SEQUENCE: 81

Gln Ser Val Leu Thr Gln Pro Pro Thr Val Ser Gly Thr Pro Gly Gln
1               5                   10                  15

Arg Val Thr Ile Ser Cys Ser Gly Ser Ser Asn Ile Gly Ser Lys
                20                  25                  30

Asn Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Leu
                85                  90                  95
```

```
Ser Gly Trp Val Phe Gly Gly Thr Lys Val Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
            210                 215

<210> SEQ ID NO 82
<211> LENGTH: 447
<212> TYPE: PRT
<213> ORGANISM: Homo sapiens

<400> SEQUENCE: 82

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Ile Leu Trp Phe Gly Glu Tyr Leu Gly Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Cys Cys
            210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 83
<211> LENGTH: 214
<212> TYPE: PRT
<213> ORGANISM: Homo sapiens

<400> SEQUENCE: 83

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr His Cys Gln Gln Tyr Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
        210

<210> SEQ ID NO 84
<211> LENGTH: 447
<212> TYPE: PRT
<213> ORGANISM: Homo sapiens

<400> SEQUENCE: 84

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
            35                  40                  45

Ile Gly Ser Ser Asn His Ser Gly Ser Thr Tyr Tyr Asn Pro Ser Leu
        50                  55                  60

Arg Ser Arg Val Thr Ile Ser Val Asp Thr Ser Lys Asn Gln Phe Ser
65                  70                  75                  80

Leu Lys Val Asn Ser Val Thr Ala Ala Asp Thr Ala Val Tyr Tyr Cys
                85                  90                  95

Ala Arg Glu Ala Gly Tyr Ser Ser Trp Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 85
<211> LENGTH: 216
<212> TYPE: PRT
<213> ORGANISM: Homo sapiens

<400> SEQUENCE: 85

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val His Glu Gly Ser Thr Val Glu Lys
        195                 200                 205

Thr Val Ala Pro Thr Glu Cys Ser
    210                 215

<210> SEQ ID NO 86
<211> LENGTH: 46
<212> TYPE: DNA
<213> ORGANISM: artificial sequence
<220> FEATURE:
<223> OTHER INFORMATION: chemically synthesized
```

-continued

```
<400> SEQUENCE: 86
cctggccggc ctggccacta gtgaccgatg ggcccttggt ggaagc         46
```